United States Patent [19]

Bonutti

[11] Patent Number: 5,542,423

[45] Date of Patent: *Aug. 6, 1996

[54] INDEXING ASSEMBLY FOR JOINT IMAGING

[75] Inventor: Peter M. Bonutti, Effingham, Ill.

[73] Assignee: Apogee Medical Products, Inc., Effingham, Ill.

[*] Notice: The term of this patent shall not extend beyond the expiration date of Pat. No. 5,329,924.

[21] Appl. No.: 237,598

[22] Filed: May 3, 1994

Related U.S. Application Data

[63] Continuation-in-part of Ser. No. 802,358, Dec. 4, 1991, Pat. No. 5,349,956, and a continuation-in-part of Ser. No. 950,600, Sep. 24, 1992, Pat. No. 5,343,580.

[51] Int. Cl.⁶ ........................................ A61B 6/00
[52] U.S. Cl. ........................... 128/653.1; 128/653.2; 128/653.5; 5/601; 5/621
[58] Field of Search ......................... 128/653.1, 653.2, 128/653.5, 882, 774, 779; 5/601, 621–624

[56] References Cited

U.S. PATENT DOCUMENTS

| | | |
|---|---|---|
| 1,239,146 | 9/1917 | Wantz . |
| 2,801,142 | 7/1957 | Adams . |
| 2,975,505 | 2/1961 | Weickgenannt . |
| 3,025,397 | 3/1962 | Travis et al. . |
| 3,124,328 | 3/1964 | Kortsch . |
| 3,521,876 | 7/1970 | Smith . |
| 3,528,413 | 9/1970 | Aydt . |
| 3,766,384 | 10/1973 | Anderson . |
| 4,050,355 | 9/1977 | Niskanen . |
| 4,232,681 | 11/1980 | Tulaszewski . |
| 4,256,112 | 3/1981 | Kopf et al. . |
| 4,291,229 | 9/1981 | Patt . |
| 4,323,080 | 4/1982 | Melhart ............................. 128/882 |
| 4,407,277 | 10/1983 | Ellison ............................. 128/882 |
| 4,562,588 | 12/1985 | Ruf . |
| 4,616,814 | 10/1986 | Harwood-Nash et al. . |
| 4,681,308 | 7/1987 | Rice . |
| 4,717,133 | 1/1988 | Walsh et al. . |
| 4,827,496 | 5/1989 | Cheney . |
| 5,001,739 | 3/1991 | Fischer . |
| 5,007,912 | 4/1991 | Albrektsson et al. . |
| 5,078,140 | 1/1992 | Kwoh . |
| 5,154,178 | 10/1992 | Shah ............................. 128/653.2 |
| 5,267,949 | 12/1993 | De La Torre et al. ............. 128/882 |
| 5,329,924 | 7/1994 | Bonutti ............................. 128/653.1 |
| 5,349,956 | 9/1994 | Bonutti ............................. 128/653.1 |

OTHER PUBLICATIONS

"Patellofemoral joint abnormalities in athletes: Evaluation by kinematic magnetic resonance imaging" by Frank G. Shellock, PhD pp. 71–95 of Topics in Magnetic Resonance Imaging/vol. 3, Issue 4, 1991.

*Primary Examiner*—Ruth S. Smith
*Attorney, Agent, or Firm*—Tarolli, Sundheim, Covell, Tummino & Szabo

[57] ABSTRACT

A self-contained apparatus is for use during imaging of a shoulder joint or hip joint of a patient, with the patient lying on an imaging table or other support movable into and out of a primary imaging coil. The apparatus includes an index mechanism having an index member lockable in any selected one of a plurality of sequential index positions. Table attachment means connects the index mechanism with the table for sliding movement with the table. A cuff support member is connected with the index member for movement with the index member. A cuff supported on the cuff support member at a location remote from the index member for clamping onto the patient's arm or leg. The cuff is connected with the support member for movement with the support member and with the index member and is lockable with the index member in any selected one of the plurality of sequential spaced index positions.

44 Claims, 14 Drawing Sheets

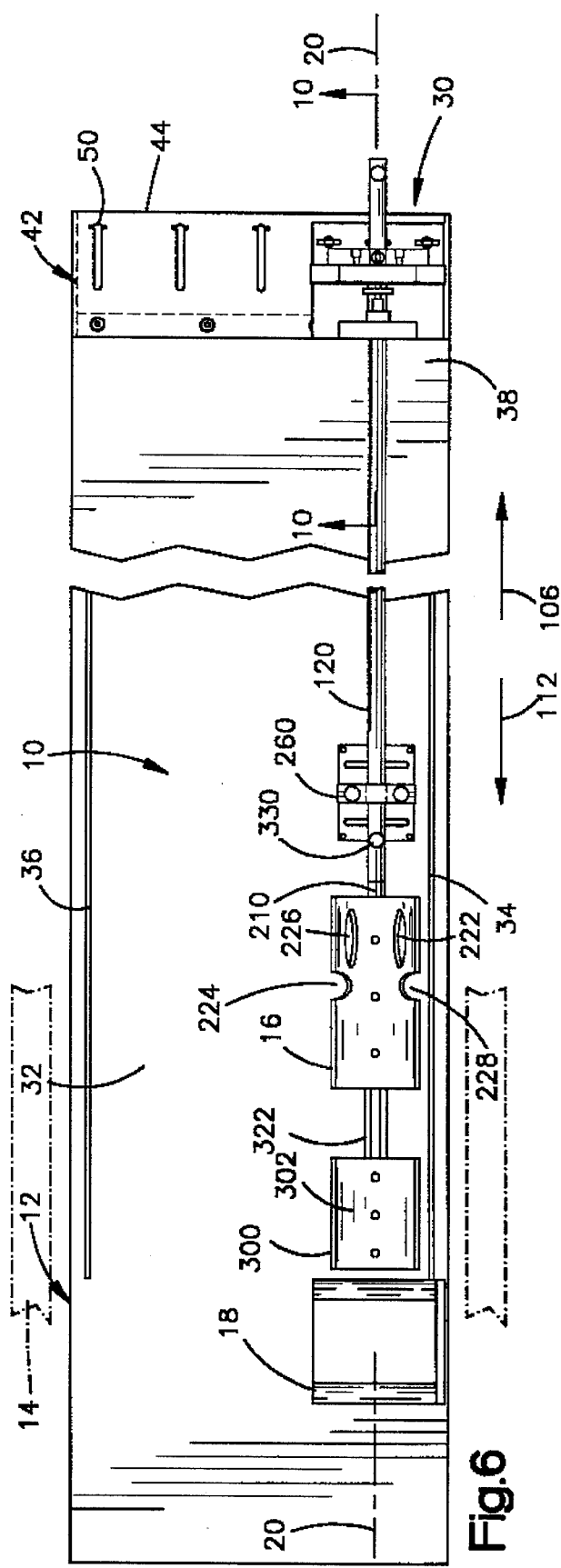
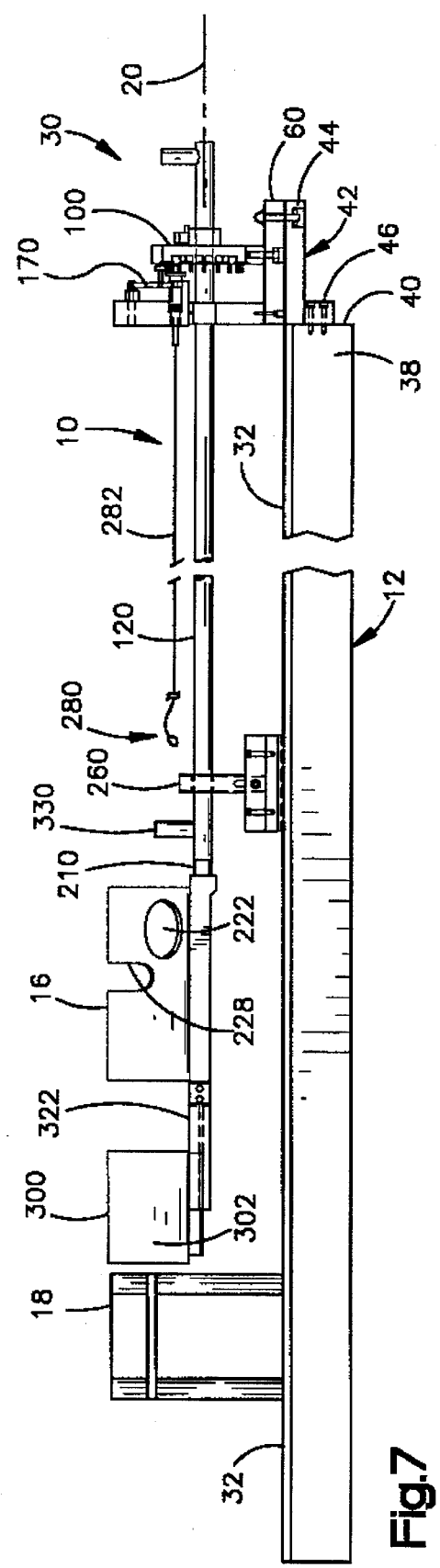

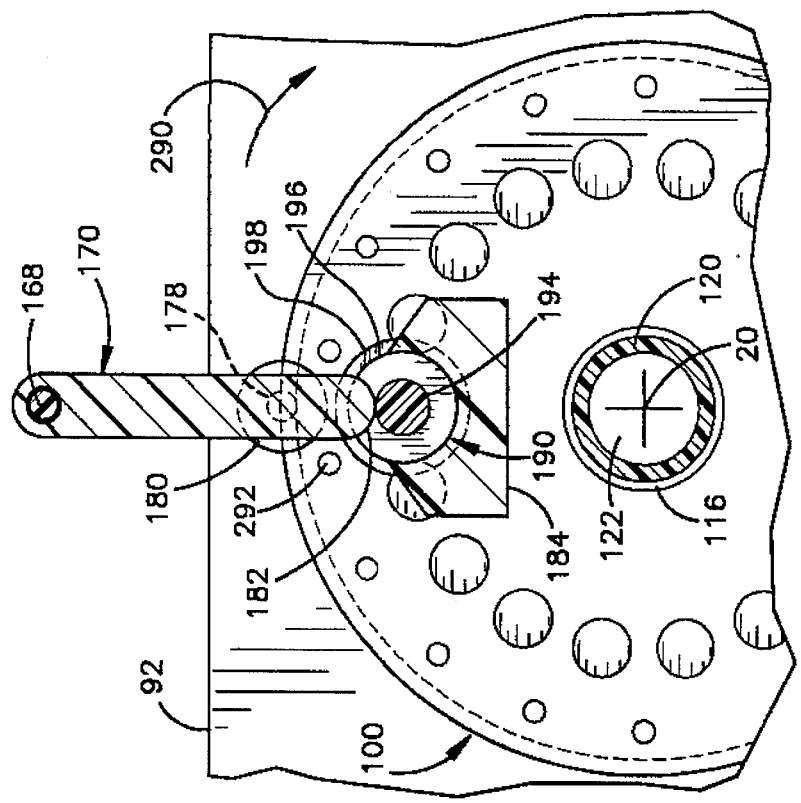
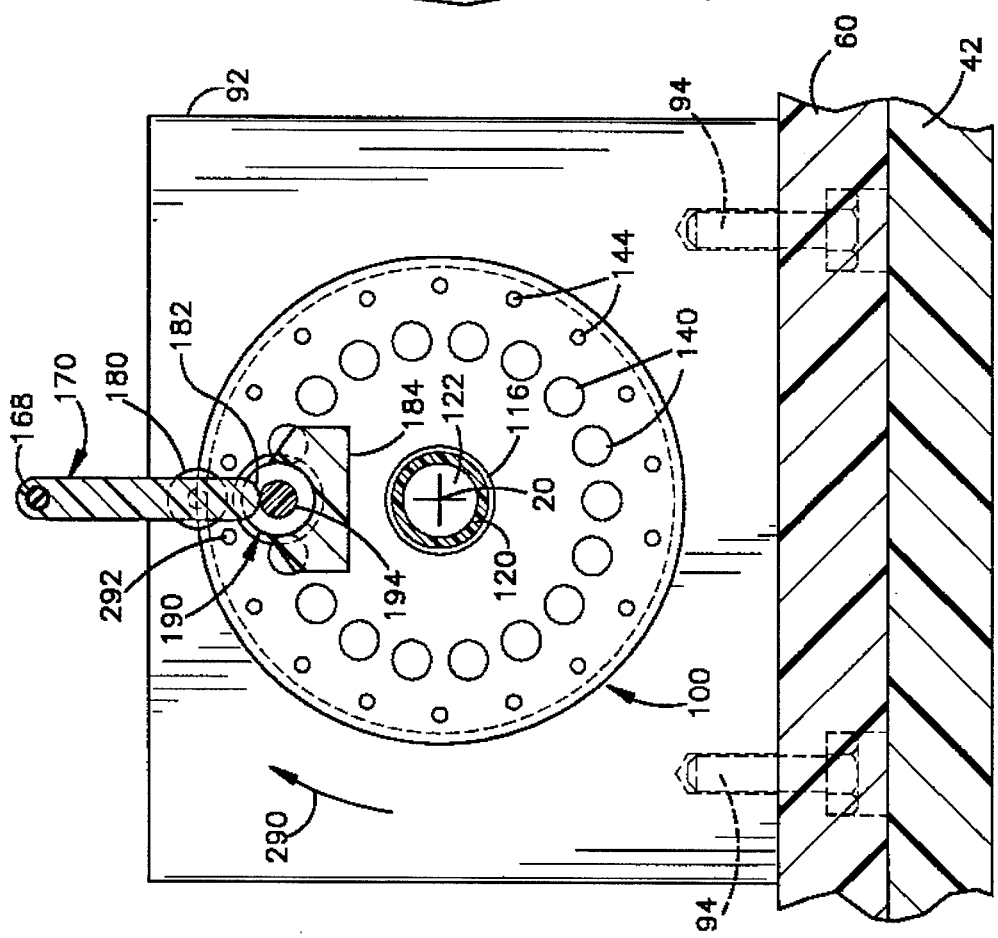

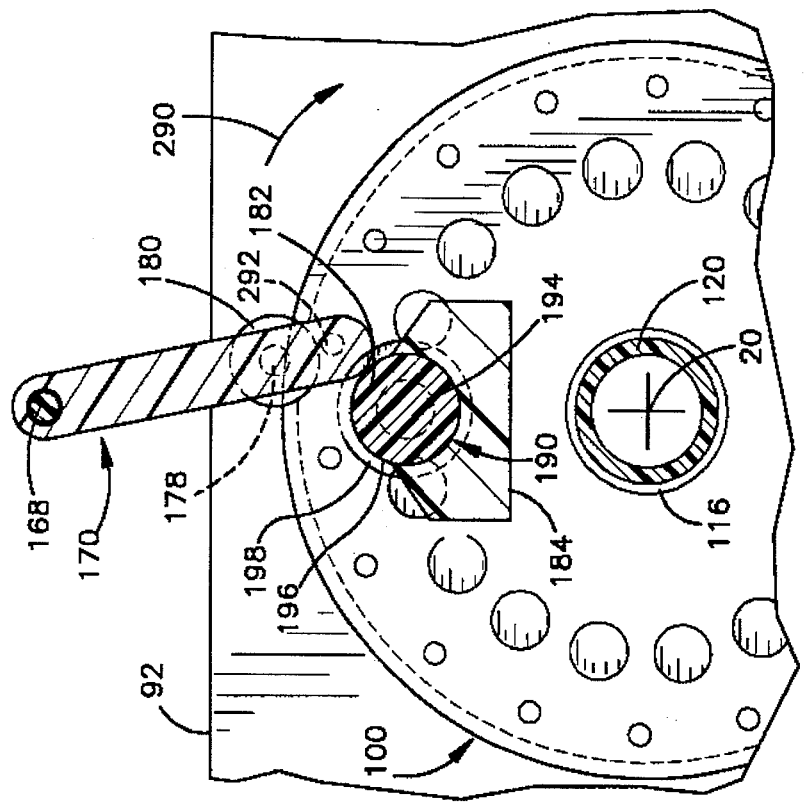
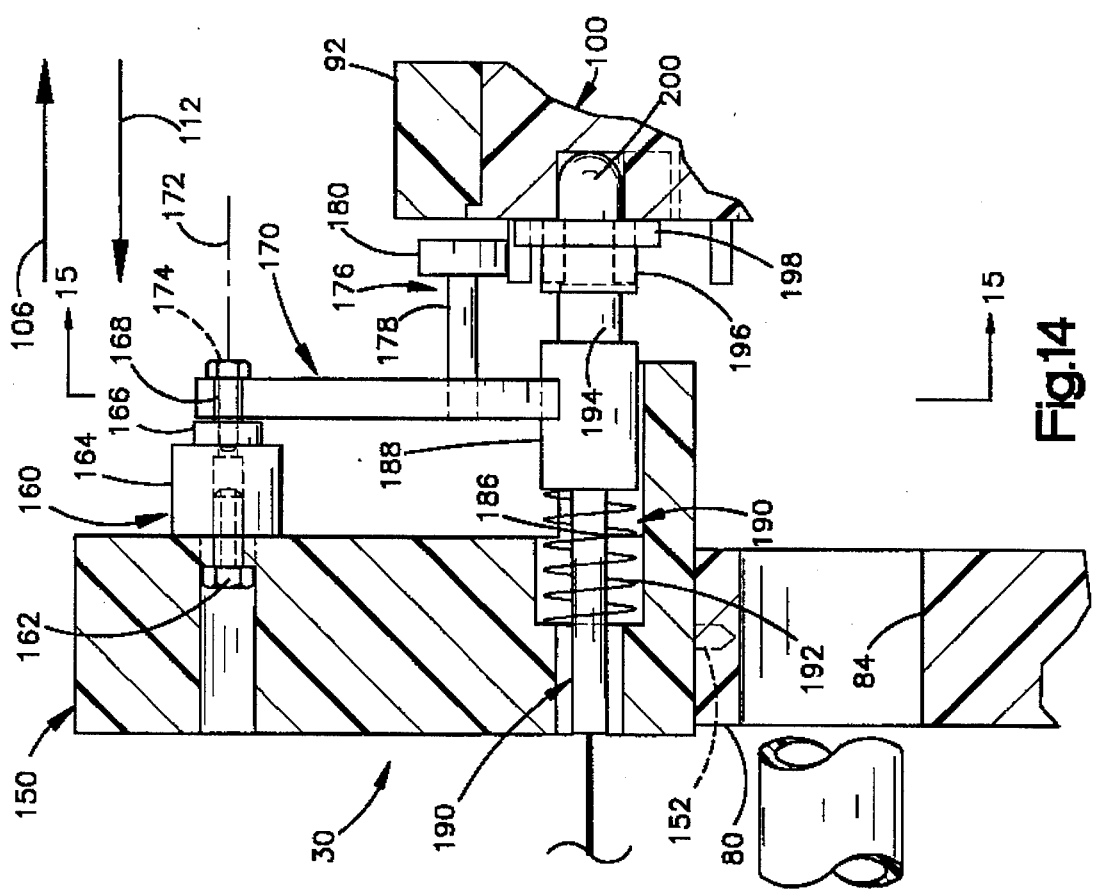

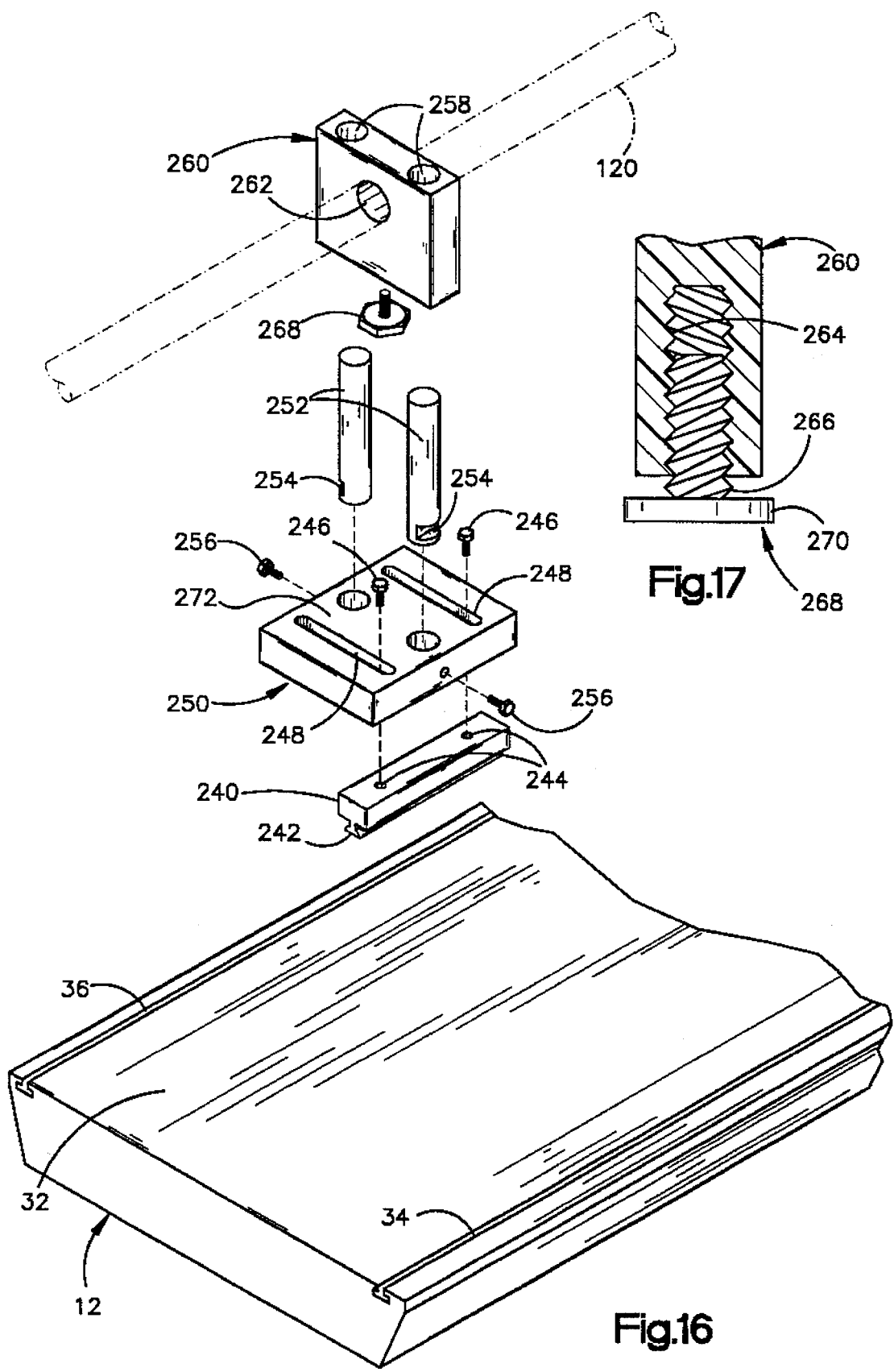

INDEXING ASSEMBLY FOR JOINT IMAGING

RELATED APPLICATIONS

This application is a continuation-in-part of U.S. patent application Ser. No. 07/802,358 filed Dec. 4, 1991, now U.S. Pat. No. 5,349,956. This application is also a continuation-in-part of U.S. patent application Ser. No. 07/950,600 filed Sep. 24, 1992, now U.S. Pat. No. 5,343,580. The benefit of the earlier filing dates of the aforementioned applications for all subject matter common to this application is hereby claimed.

BACKGROUND OF THE INVENTION

The present invention relates to an indexing assembly for use in imaging of a joint in the human body. In the one embodiment, the present invention is an indexing assembly for use in moving a shoulder or hip joint through its range of motion during imaging of the joint in a magnetic resonance imaging ("MRI") apparatus.

Static imaging of a joint, that is imaging of the joint in only one orientation, may not disclose joint abnormalities or defects which are visible in kinematic imaging of the joint. Kinematic imaging of the joint takes a series of images of the joint at different orientations of the joint.

It would be desirable to have an indexing assembly for use in imaging in a primary MRI coil which provides the capability of accurate and repeatable kinematic indexing a joint such as a shoulder or hip joint. The indexing assembly should preferably be patient directed.

SUMMARY OF THE INVENTION

The present invention is an apparatus and method for use in medical imaging. The present invention provides a system to simulate within an imaging coil normal movements of body parts such as joints, and to improve imaging of soft tissue and bony parts as compared to a static system in which images are taken of a joint in only one position.

In accordance with a first aspect of the present invention, there is provided controlled motion of a limb, while in an imaging coil, either patient directed or operator directed. The limb is moved into various positions in multiple planes within its range of motion while a series of images are taken of a joint region where the limb is connected with a trunk of the patient. These individual images may then be collated into a cine format to effectively show the joint in motion. Thus, the present invention allows for studying a joint in motion and also allows for studying a joint or other body part at any positions within its range of motion allowable within the confines of the primary coil.

In accordance with another aspect of the present invention, traction is applied to a joint being imaged, in order to load the joint. This can simulate normal loading of a joint. Distracting a joint can also allow a better view of the parts of the joint and thus an increased imaging benefit. It can also allow simulation of normal loading of a joint, such as when carrying a heavy object or performing an athletic or work-related task. Traction can also be applied to a joint being imaged when the joint is in various positions, to simulate normal loading of a joint within its range of motion.

A self-contained shoulder or hip indexing apparatus is for use during imaging of a joint of a patient, with the patient in a primary imaging coil. The self-contained indexing apparatus includes an index mechanism having an index member lockable in any selected one of a plurality of sequential index positions. A cuff support member is connected with the index member for movement with the index member. A cuff supported on the cuff support member grips the patient's hand/or arm where a shoulder joint is being imaged. The cuff grips the patient's leg when a hip joint is being imaged. The cuff is connected with the support member for movement with the support member and with the index member and is lockable with the index member in any selected one of the plurality of sequential spaced index positions.

BRIEF DESCRIPTION OF THE DRAWINGS

The foregoing and other features of the present invention will become apparent to one skilled in the art to which the present invention relates upon consideration of the following description of the invention with reference to the accompanying drawings, wherein:

FIG. 6 is a top plan view of an apparatus for use in imaging a joint region in accordance with the method of the present invention, the apparatus includes a support for use inside a primary imaging coil of a magnetic resonance imaging apparatus;

FIG. 7 is a side elevational view of the apparatus of FIG. 1;

FIG. 12 is a transverse sectional view taken along line 12—12 of FIG. 10;

FIG. 13 is an enlarged view of a portion of FIG. 12;

FIG. 14 is an enlarged view, similar to FIG. 11, showing the index assembly in a locked condition;

FIG. 15 is an enlarged view, taken along line 15—15 of FIG. 14, showing the index assembly in a locked condition;

FIG. 16 is an exploded perspective view of a free guide assembly which is part of the apparatus of FIG. 6;

FIG. 17 is an enlarged view of a portion of the free guide assembly of FIG. 16;

DESCRIPTION OF PREFERRED EMBODIMENTS

Figure 1:
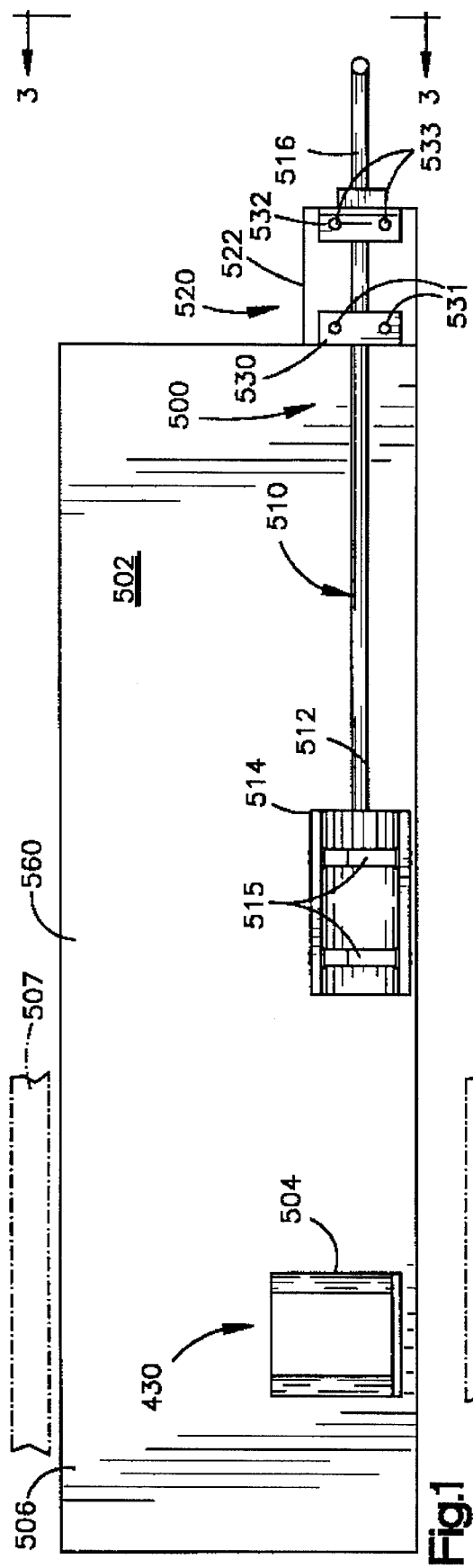
FIG. 1 is a top plan view of an apparatus for use in imaging a joint region in accordance with the method of the present invention.
Figure 2:
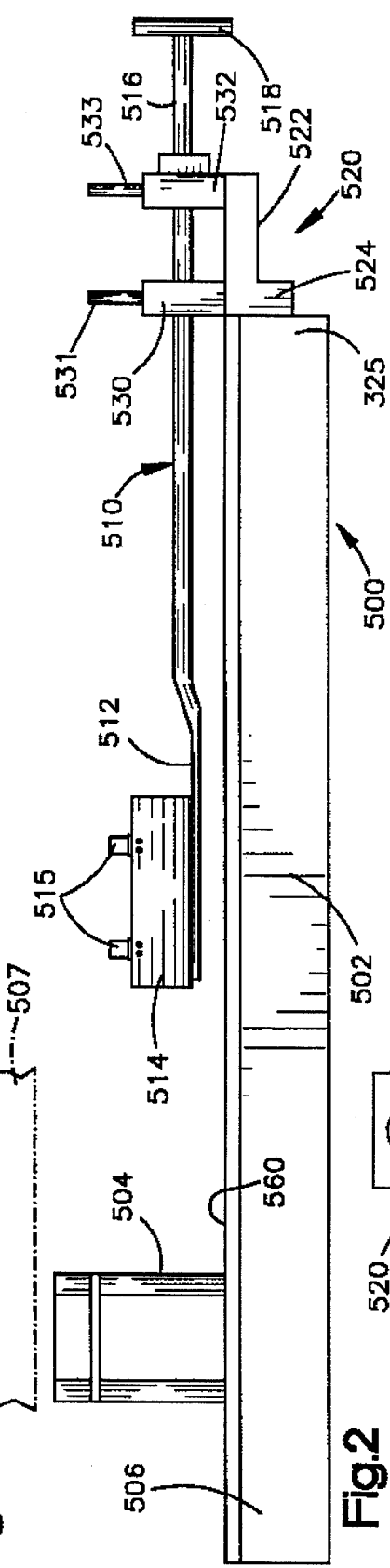
FIG. 2 is a side elevational view of the apparatus of FIG. 1.
Figure 3:
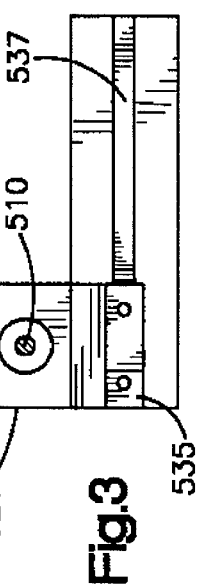
FIG. 3 is a partial end view, taken along the line 3—3 of FIG. 1.

An apparatus 500 for use in imaging a joint region where an upper portion of a limb of a patient is connected with a trunk of a patient is illustrated in FIGS. 1 and 2. Thus, the apparatus 500 may be adapted to image either a shoulder joint region or a hip joint region of a patient. In the embodiment illustrated in FIGS. 1 and 2, the apparatus 500 is adapted to image a shoulder joint region of a patient.

The apparatus 500 is mounted to an imaging table 502 which may be the imaging table disclosed in U.S. patent application Ser. No. 07/802,358 filed Dec. 4, 1991 or may be a known imaging table. If desired, the patient could be supported on an apparatus other than a table. A known secondary imaging coil 504 is secured to the table 502 by suitable means. The coil is located in a position for imaging a particular body part. As illustrated in FIGS. 1 and 2, the coil 504 is positioned to image a shoulder of a patient who is lying on the table 502 with his head adjacent the end 506 of the table 502.

The apparatus 500 includes a rotatable support rod or member 510 extending longitudinally along the table 502 from a position over the table and inside a primary coil 507 (FIG. 1) to a position off the end of the table 502 and outside the coil 507. The rod 510 has an inner end portion 512 to which is fixed an attachment member 514. The member 514 may be any suitable apparatus, such as a cuff, for attachment to a body part such as a forearm, for example, and may include means, such as straps 515, for securing the cuff to the body part for movement therewith. The rod 510 also has an outward end portion 516 to which is attached a handle 518 for rotational and longitudinal movement of the rod 510 by a person other than the patient (not shown).

Figure 4:
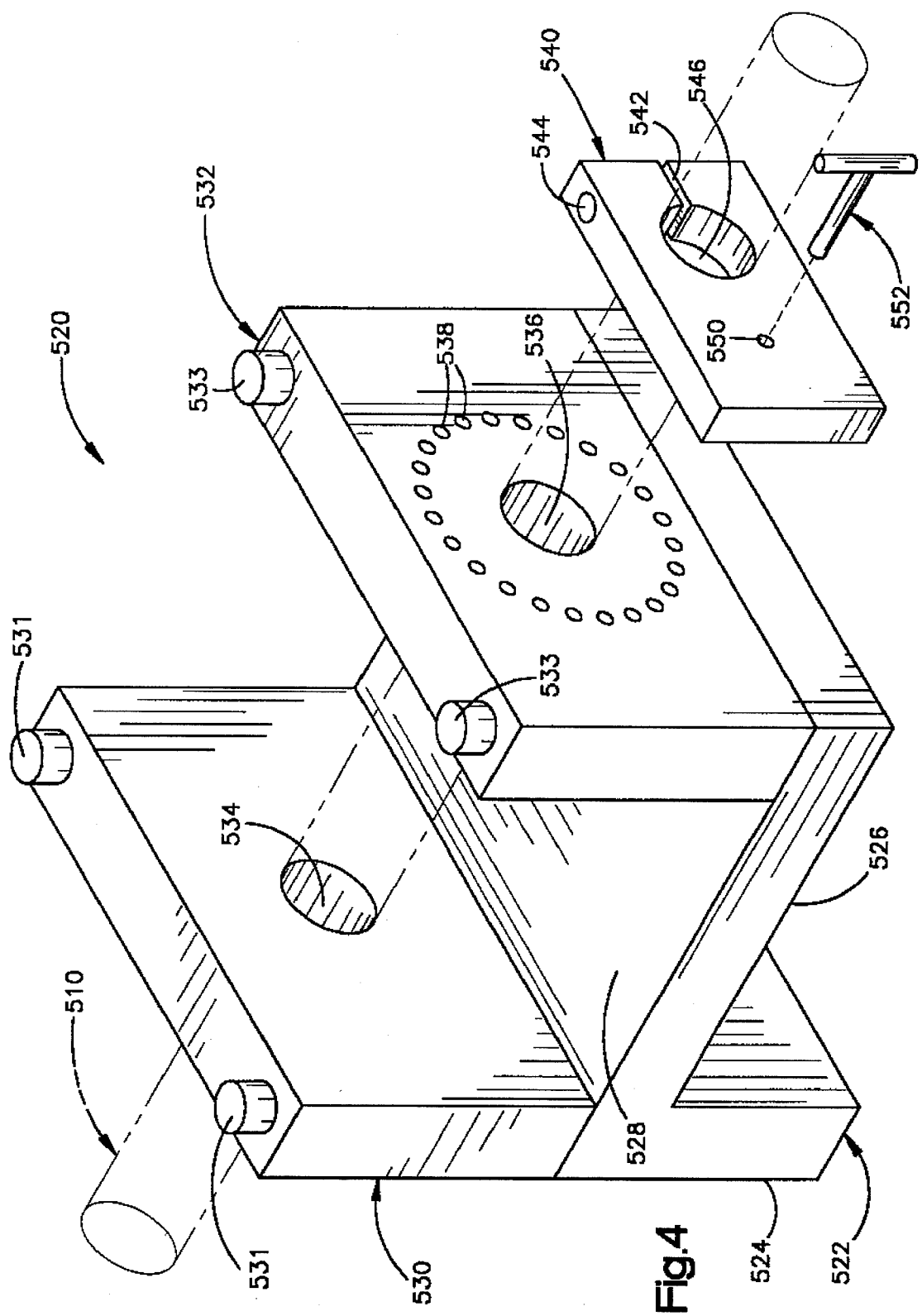
FIG. 4 is an enlarged perspective view of a portion of the apparatus of FIG. 1.

The rod 510 extends through and is positioned by an index mechanism 520, better seen in FIG. 4. The index mechanism 520 includes a base 522 having a first leg portion 524 (FIG. 4) and a second leg portion 526. The leg portion 524 is fixed to the table 502. The leg portion 526 (FIG. 4) has an upper major side surface 528 to which are attached support blocks 530 and 532. The support block 530 has an opening 534 through which the rod 510 extends and is movable. The support block 532 has an opening 536, aligned with the opening 534, through which the rod 510 also extends and is movable. The blocks 530 and 532 support the rod 510, and thus the cuff 514. The block 532 also has a plurality of index openings 538 (FIG. 4). The index openings 538 are spaced regularly in a circle around the rod 510.

An index block 540 is disposed on the rod 510 outside the block 532. The rod 510 extends through an opening 546 in the index block 540. The index block 540 includes a split clamp portion 542 and a clamping bolt 544. When the split clamp 542 is loosened, the index block 540 is rotatable on and movable longitudinally on the rod 510. When the split clamp 542 is tightened, the block 540 is fixed for movement with the rod 510.

The index block 540 has an index pin opening 550 through which is extensible an index pin 552 (FIG. 4). The opening 550 is the same distance from the center of the opening 546, as the index openings 538 are from the center of the opening 536 in the block 532. Thus, the index pin opening 550 is alignable with any selected one of the index openings 538 on the support block 532 by a person other than the patient.

When the opening 550 is aligned with one of the index openings 538, the index pin 552 may be inserted through the index pin opening 550 and into the selected index opening 538, to block rotation of the index block 540 relative to the support block 532. If the index block 540 is clamped firmly to the rod 510, this blocks rotational movement of the rod 510 relative to the support block 532. Since the support block 532 is fixed to the table 502, this therefore blocks rotational movement of the rod 510 relative to the table 502, also thus fixing the cuff 514 in position.

Figure 5:
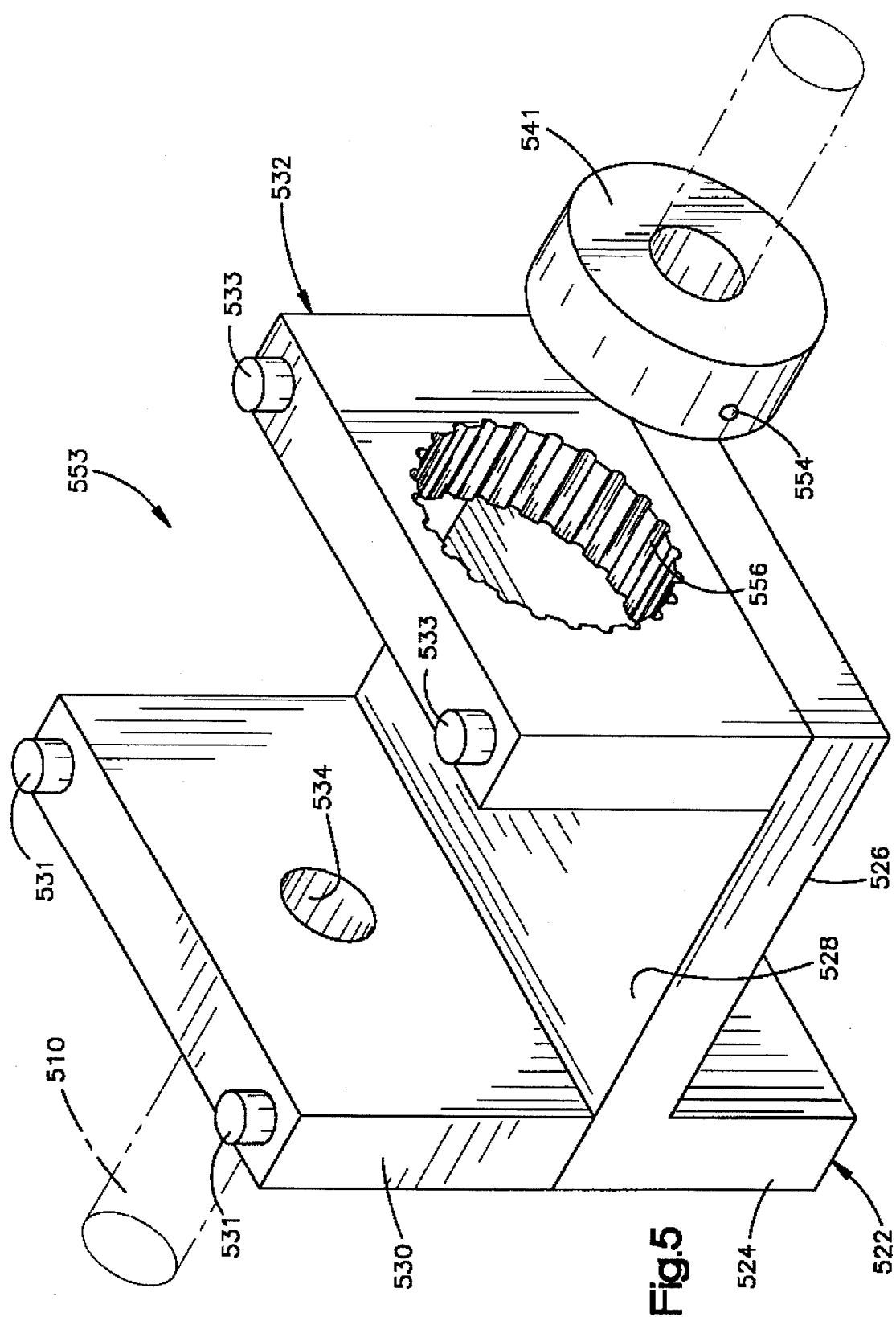
FIG. 5 is an enlarged perspective view, generally similar to FIG. 4, showing an alternate embodiment of a portion of the apparatus of FIG. 1.

It should be noted that other indexing mechanisms may be provided to replace the index pin opening 550 and index pin 552. For example, as shown in FIG. 5, index block 541 of an index mechanism 553 may have a spring loaded ball 554 on its radially outer surface facing the support block 532, which is selectively engageable at one of a plurality of ribbed index locations 556, thus functioning as a detent mechanism. This is suitable for a patient-directed operation.

If the apparatus 500 (FIGS. 1 and 2) is to be patient directed, the portion of the rod 510 extending outwardly past the index mechanism 520 may be omitted. The patient adjusts the index mechanism by moving the body part, thus moving the cuff and support rod. Other index constructions are equally feasible. However, if the apparatus 500 is to be directed by an operator other than the patient, the operator applies force to the handle 518 (FIG. 2) to release the index ball 554 (FIG. 5) and rotate the rod 510.

In operation of the apparatus 500, the patient is first placed on a support surface 560 (FIGS. 1 and 2) on the table 502 in a position as desired. The coil 504 is adjusted so as to properly image the body part in question. (It should be noted that use of a secondary coil such as the coil 504 is not essential to functioning or use of the apparatus 500.)

The cuff 514 is then attached to a portion of the patient's body at a location selected to be able to move the body part to be imaged into a plurality of different positions. For example, if a shoulder joint region is to be imaged, then the cuff 514 may be attached to the patient's forearm. The rod 510 then forms an extension of the patient's arm. Movement of the patient's forearm by means of the rod 510 and handle 518 will then cause the shoulder joint to move between a plurality of different orientations. Rotation of the patient's arm, by the patient, about the central axis of the arm is effective to rotate the cuff 514. Force applied to the cuff by the patient's arm is transmitted through the cuff to the rod 510 to rotate the rod.

Similarly, if the patient's hip is to be imaged, the cuff 514 may be attached to the patient's leg, for example, the lower leg. Movement of the cuff 514 will cause movement of the hip joint to a plurality of different orientations in which it may be sequentially imaged. Rotation of the patient's leg, by the patient, about the central axis of the leg is effective to rotate the cuff 514. Force applied to the cuff by the patient's leg is transmitted through the cuff to the rod 510 to rotate the rod.

The rod 510 as noted is longitudinally movable by pulling or pushing on the handle 518. Thus, as the imaging operator moves the handle 518 longitudinally relative to the table 502, the cuff 514 thus moves longitudinally also. The operator can therefore control the longitudinal position of the cuff 514, and of its attached body part, from a location exterior to the primary coil.

By pulling on the rod 510, the operator can distract a joint of the patient. Thus, when the cuff 514 grips an arm of a patient, the operator can pull on the handle 518 to move the rod 510 axially toward the right (as viewed in FIGS. 1 and 2) to distract the shoulder joint of the patient. When the cuff 514 grips a leg of a patient, the operator can pull on the handle 518 to move the rod 510 axially toward the right (as viewed in FIGS. 1 and 2) to distract the hip joint of the patient.

The rod 510 is also rotatable, by means of the handle 518. The operator rotates the handle 518 to position the cuff 514 and its attached body part in the desired orientation for imaging. This rotational position is then locked in by means of the index assembly 520. It should be noted that any number, location, or sequence of index locations 538 may be provided. Those shown are illustrative only. In fact, an index assembly may be provided which can be locked in any rotational position within a full circle.

Many joints are movable in multiple degrees of freedom. The shoulder joint, for example, is movable in four degrees of freedom (or multiple planes of movement). In order to fully understand the joint anatomy, it is desirable to be able to image a joint in all these possible positions. Accordingly, the present invention provides for movement of a positioning apparatus such as the cuff 514 not merely rotationally and longitudinally, but also up and down and sideways.

Thus, as seen in FIGS. 1-5, the apparatus 500 may be made movable up and down and also sideways relative to the table 502. The index blocks 530 and 532 are movable up and down along rods 531 and 533 (FIG. 4), respectively, which rods are fixed to the base block 522. Thus, the support rod 510 (FIGS. 1 and 2) and cuff 514 can be moved up and down to provide a third degree of movement in addition to the rotation and longitudinal movement available. Further, the index assembly 520 has a guide member 535 (FIG. 3) engaging in a slot 537. Thus, the index assembly is movable sideways along the table 502 (FIGS. 1 and 2) to carry the support rod 510 and the cuff 514 in a fourth degree of movement. With these multiple degrees of movement, in multiple planes, it is now possible to move a joint into almost any position to simulate natural joint movement, while within an imaging coil.

Another feature of the present invention is that traction can be applied to a joint being imaged, in order to distract the joint. For example, in the apparatus illustrated in FIGS. 1-5, traction can be applied to a joint by pulling outwardly (to the right as viewed in FIGS. 1 and 2) on the rod 510. Such force when applied to the rod 510 acts through the cuff 514 on the joint being imaged. Distracting a joint can allow a better view of the parts of the joint and thus an increased imaging benefit. This feature is not available with present imaging apparatus.

It should be noted that additional body part attachments are possible in order to better control movement and positioning. For example, extra cuffs or clamps, in addition to the one cuff shown in the drawings, may be attached to the body to more carefully and tightly control its movement and positioning. Further, it should be understood that other types of cuffs may be used, such as inflatable cuffs, etc. The cuffs should further be designed so that there is no plastic in contact with the skin. Such contact causes sweating and perspiration build up which causes imaging aberrations. Accordingly, a material is preferably provided against the skin to wick the perspiration away.

Accordingly, it is seen that the present invention provides an apparatus for longitudinally and rotationally positioning a body part so as to control the position or orientation of a joint connected with the body part. This positioning is independently controllable by the operator from a location external to the primary coil. This positioning requires no physical support effort by the patient during the time period of the imaging, since the rod positioning apparatus fully supports the weight of the body part connected therewith.

Nor does this adjustable positioner require any effort on the part of the patient to maintain the selected position, as the apparatus 500 performs that function also. A plurality of sequential images may be taken of a joint, for example, in differing positions, without undue effort on the part of the patient. (It should be noted that patient control of any of the positioning apparatus of the present invention is possible, as well as the described operator control.)

In view of the foregoing description it is apparent that the present invention provides an apparatus 500 and method for use in imaging a joint region where a limb of a patient is connected with a trunk of the patient. Thus, the apparatus 500 and method of the present invention may be used to image a shoulder joint region in a chamber of the primary coil 507 of an imaging unit. The apparatus 500 and method of the present invention may also be used to image a hip joint region in the chamber of the primary coil 507.

The cuff 514 is connected with the limb of the patient, that is, either the arm or leg of the patient. The table 502 is moved into the chamber of the primary coil 507 of a magnetic resonance imaging unit. The orientation of at least a portion of either the shoulder or hip joint region is changed while the shoulder or hip joint region is in the chamber of the primary coil 507 of the magnetic resonance imaging unit.

The orientation of a portion of the hip or shoulder joint region is changed by rotating the cuff 514 and limb about an axis of the limb which extends through the joint region. Thus, when the cuff 514 is attached to the arm of a patient, the cuff and arm are rotated together about the central axis of the arm and the rod 510 to change the orientation of the shoulder joint region of the patient while the shoulder joint region is in the magnetic resonance imaging unit. Similarly, when the cuff 514 is attached to the leg of a patient, the cuff and leg are rotated together about the central axis of the leg and the rod 510 to change the orientation of the hip joint region of the patient while the hip joint region is in the magnetic resonance imaging unit.

Upon rotation of the limb of the patient and the rod 510 to a first predetermined position, the index mechanism 520 (FIG. 4) of the index mechanism 553 (FIG. 5) is operated to an engaged condition to retain the rod in the first predetermined position. The index mechanism 520 (FIG. 4) is operated to the engaged position by a person, other than the patient, inserting the index pin 552 into one of the index openings 538. The index mechanism 553 is automatically operated to the engaged condition by the spring loaded ball 554 engaging an index location 556. The limb and the rod 510 may be rotated to the first predetermined position either prior to or after movement of the joint region into the magnetic resonance imaging unit.

After the joint has been imaged, the index mechanism 520 or 530 is operated to a disengaged condition to release the rod 510 and cuff 514 for rotation to a next succeeding imaging position. The index mechanism 520 is released by an operator removing the index pin 552 from an opening 538. The index mechanism 553 is released by the patient applying force to the cuff 514 with the limb which is gripped by the cuff. This force is transmitted to the rod 510 to rotate the rod and force the spring loaded ball 554 to a retracted position. When the rod 510 is moved to the next imaging position, the index mechanism 520 or 553 is re-engaged. These steps are repeated to effect sequential imaging of a joint region while the joint region remains in the chamber of the primary coil 507 of the magnetic resonance imaging unit.

To change the orientation of at least a portion of the joint region in the imaging unit, the cuff 514 and rod 510 are rotated. The cuff 514 and rod 510 may be rotated under the influence of force applied against the cuff by the limb of the patient. Alternatively, the cuff 514 and rod 510 may be rotated under the influence of force applied against the handle 518 by an operator.

FIG. 6 illustrates an index assembly 10 for use in imaging the shoulder of a joint of a patient (not shown). The index assembly 10 is described in detail below, as is its operation. The patient lies on a known support or imaging table 12 which is slidable into and out of a known primary imaging coil 14 shown schematically in FIG. 6. If desired, the patient could be supported on an apparatus other than the table 12.

When a table is used to support the patient, the patient lies on his back, with his head to the left and his feet to the right (as viewed in FIGS. 6 and 7). The patient's right hand is secured in a cuff 16, with the palm facing up. The patient's shoulder is disposed inside a known shoulder coil 18. To provide sequential imaging of the shoulder joint, a patient rotates his hand and arm about an axis 20. The rotation of the hand and arm, and the placement of the shoulder joint in the sequential index positions spaced apart a known number of degrees are facilitated by an index mechanism 30 which is part of the overall indexing assembly 10.

The imaging table 12 is generally flat, having an upper major side or support surface 32 on which the patient lies. A support surface other than the imaging table 12, for example, a chair, may be used. The imaging table 12 has two grooves 34 and 36 (FIG. 6) in its upper major side surface 32. The grooves 34 and 36 extend longitudinally along the table 12 for the length of the table, near the outer longitudinal edges of the table. The table 12 has an end portion 38 near or supporting the patient's feet, to the right as viewed in FIGS. 6 and 7.

The table end portion 38 has an end surface 40 (FIG. 7) to which is attached a table extension 42. The table extension 42 is made of two parts, an upper portion 44 and a lower portion 46, held together by suitable fasteners (not shown). Four screws 48 (FIG. 10) extend through the table extension lower portion 46 into the table end portion 38, to secure the table extension 42 to the table 12. The table extension 42 may alternatively be made of one part only, if feasible.

Figure 9:
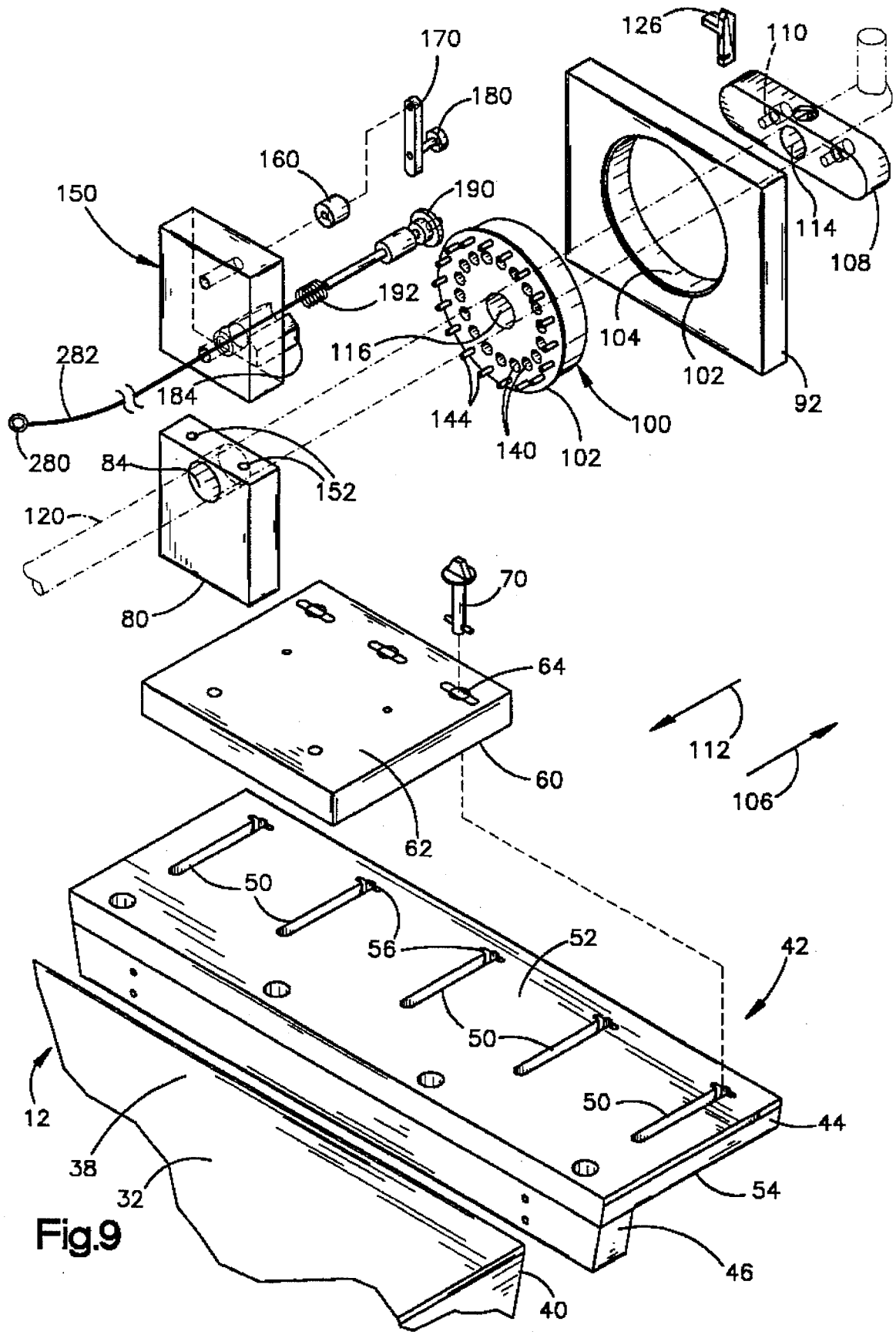
FIG. 9 is an exploded perspective view of the index assembly of FIG. 8.

The table extension 42 has five longitudinally extending slots 50 (FIG. 9). The slots 50 extend downward through the upper portion 44 of the table extension 42, from its upper major side surface 52 to its lower major side surface 54. Each slot 50 has a keyhole opening 56 at its outer end.

An indexer base 60 is disposed on the upper major side surface 52 of the table extension 42. The indexer base 60 has an upper major side surface 62. Three keyhole openings 64 extend vertically through the indexer base 60.

A hold-down 70 extends through a selected one of the keyhole openings 64 in the indexer base 60, and into one of the slots 50 in the table extension 42. A cross-pin 72 at the lower end of the hold-down 70 is received in a widened slot portion 74 in the table extension 42. When the hold-down 70 is rotated 90°, the hold-down secures the indexer base 60 to the table extension 42.

Figure 10:
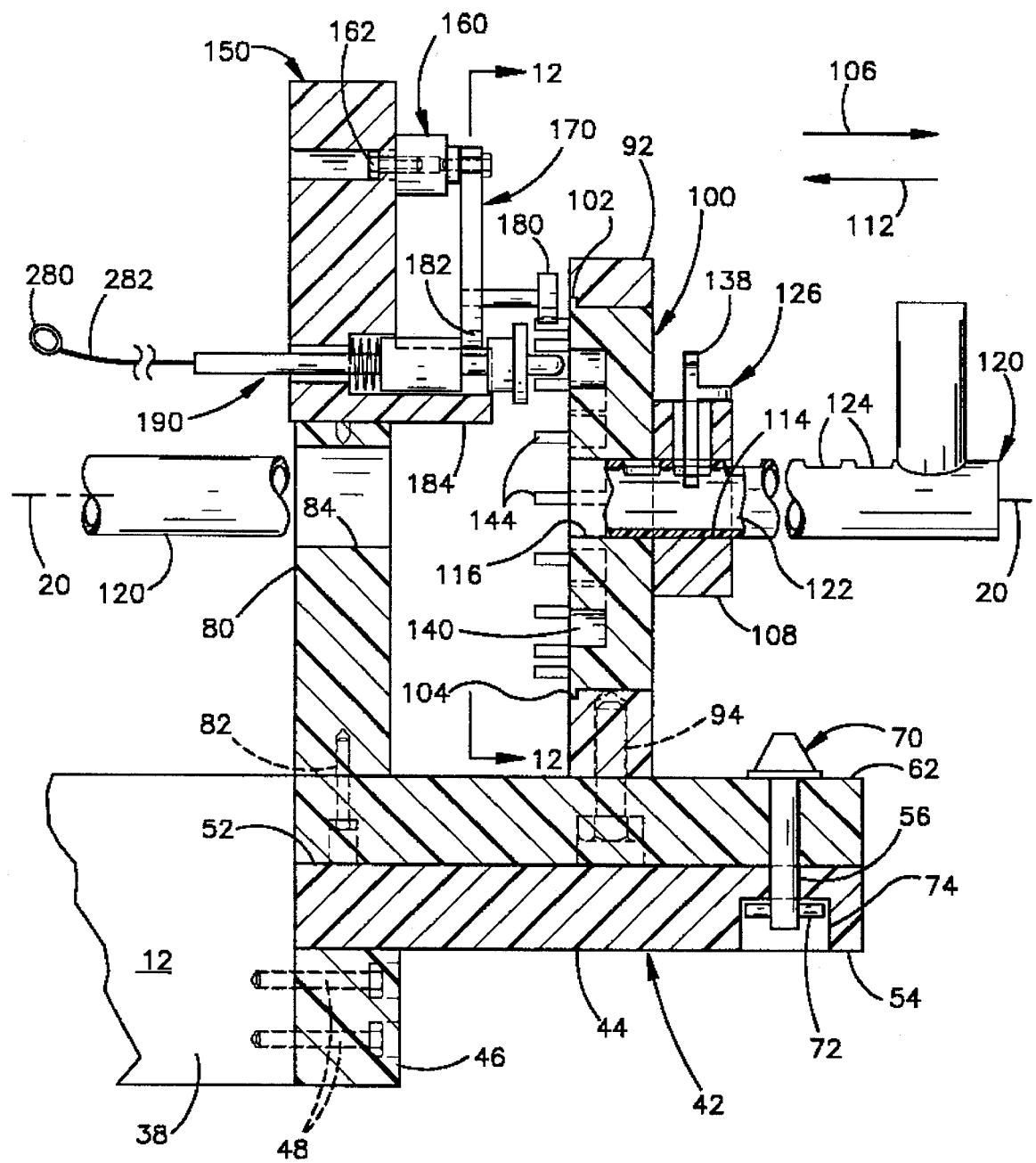
FIG. 10 is a longitudinal sectional view, taken along the line 10—10 of FIG. 6, of the index assembly.

A fixed guide 80 (FIGS. 9 and 10) is located on the upper major side surface 62 of the indexer base 60 at its inner end (to the left as viewed in FIG. 10). Two screws 82 extend up through the indexer base 60 into the fixed guide 80, to secure the fixed guide 80 to the indexer base 60. The fixed guide 80 has a central passage 84.

An indexer body 92 (FIGS. 9 and 10) is also disposed on the upper major side surface 62 of the indexer base 60. Two screws 94 extend up through the indexer base 60 into the indexer body 92 to secure the indexer body to the indexer base.

Figure 8:
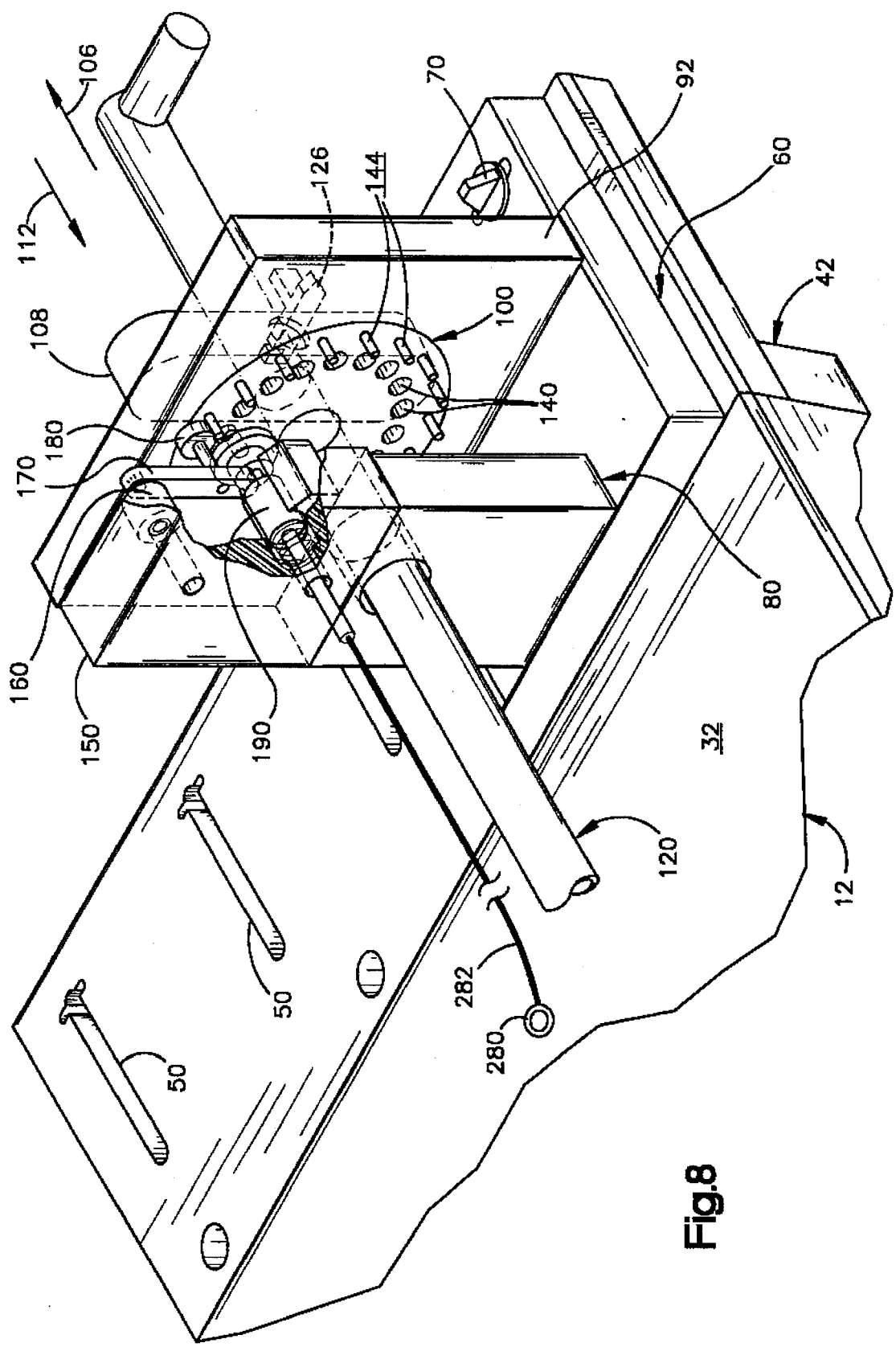
FIG. 8 is an enlarged perspective view of a portion of an index assembly used in the apparatus of FIG. 1.

An index disk 100 (FIGS. 8, 9 and 10) is rotatably received in the indexer body 92. The index disk 100 has a radially outwardly extending lip 102 (FIGS. 10 and 11) engaged against a shoulder 104 (FIG. 11) on the indexer body 92. The engagement of the index disk lip 102 with the shoulder 104 blocks axial movement of the indexer disk 100 relative to the indexer body 92, in a direction from the patient's head toward the patient's foot—i.e., to the right as viewed in FIGS. 6–10 as indicated by the arrow 106 in FIGS. 8 and 10. The index disk 100 is circular in shape and is rotatable about the axis 20, within the indexer body 92.

A clamp block 108 (FIGS. 9 and 10) is fixed to the index disk 100 for rotation with the index disk. Two screws (not shown) extend through counterbored openings 110 (FIG. 9) in the clamp block 108 and into the index disk 100, to secure the clamp block to the index disk. The length of the clamp block 108 is greater than the diameter of the index disk 100. The clamp block 108 thus blocks axial movement of the index disk 100 relative to the indexer body 92, in a direction from the patient's foot toward the patient's head—i.e., to the left as viewed in FIGS. 6–10, as indicated by the arrow 112 in FIG. 10. A central passage 114 in the clamp block 108, and a central passage 116 in the index disk 100, are coaxial with the central passage 84 in the fixed guide 80.

A rotatable support tube or member 120 extends through the coaxial aligned openings 114, 116, and 84. The support tube 120 is hollow and has a longitudinally extending central passage 122. A series of locking slots 124 (FIGS. 10 and 11) are formed in the support tube 120, extending through the wall of the support tube into the central opening 122.

Figure 20:
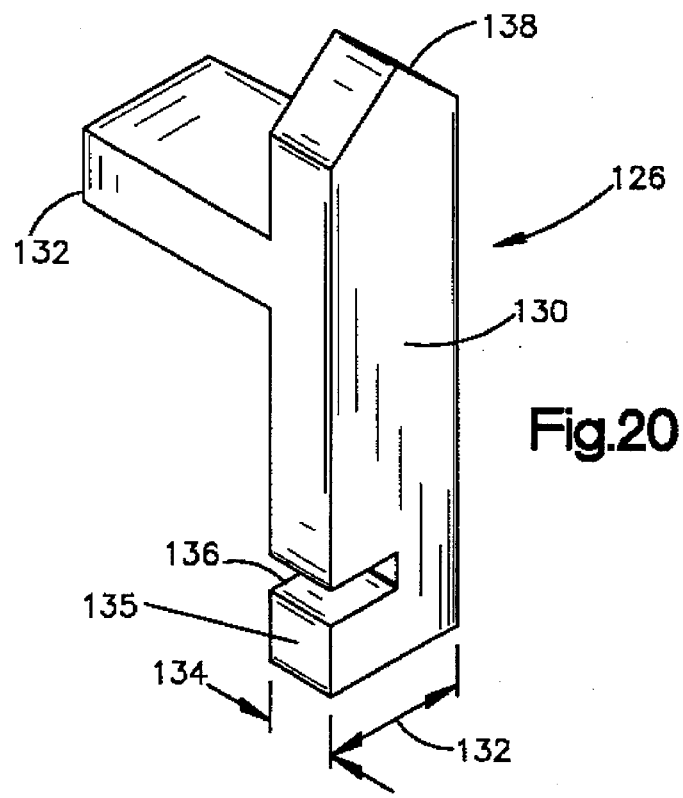
FIG. 20 is an enlarged view of a locked pointer portion of the apparatus of FIG. 6.
Figure 21:
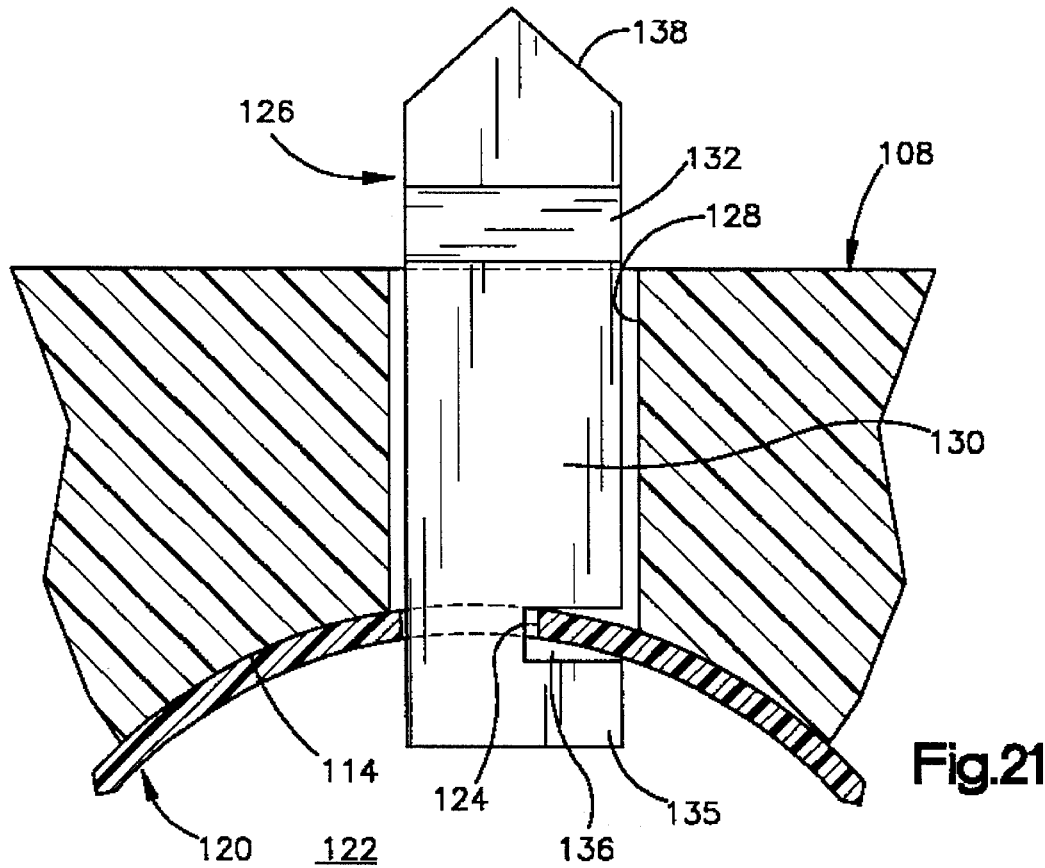
FIG. 21 is an enlarged view showing the locked pointer of FIG. 20 in engagement in the index assembly.

A lock pointer 126 (FIGS. 20 and 21) extends through an opening 128 (FIG. 21) in the clamp block 108, and through a selected one of the locking slots 124 in the support tube 120, and into the central passage 122 in the support tube. The lock pointer 126 has a main body portion 130 (FIG. 20) which is rectangular in cross-sectional configuration. The main body portion 130 has a longer dimension 132 and a shorter dimension 134. The longer dimension 132 of the lock pointer body portion 130 is slightly shorter than the diameter of the opening 128 of the clamp block 108. The lock pointer 126 has a handle portion 132. The lock pointer 126 also has a lower end portion 135 separated from the main body portion by a notch 136. The lock pointer also has a pointed outer end portion 138.

The lock pointer 126 is inserted through the opening 128 (FIG. 21) in the clamp block 108, in a rotational position such that the narrow dimension 134 of the lock pointer 126 fits through one of the slots 124 in the support tube 120. The lower end portion 135 is moved radially to a location inside the tube 120. The lock pointer 126 is then rotated so that the notch 136 engages around the wall of the support tube 120, thus locking the clamp block 108 to the support tube 120.

The pointed outer end portion 138 of the lock pointer 126 serves as an indicator to tell an MRI technician the rotational position of the support tube 120 (and of the cuff 16 which is fixed to the support tube). In the preferred embodiment, when the cuff 16 is opened upwardly as shown in FIGS. 6 and 7, the pointed outer end portion 138 of the lock pointer 126 is pointing vertically, and the clamp block 108 extends horizontally.

The index disk 100 has a set of plunger openings 140 (FIGS. 8–13) disposed in a circular array about the axis 20 (FIG. 12). The plunger openings 140 extend axially part way into the index disk 100 (FIG. 11) in a direction as indicated by the arrow 106. The index disk 100 also has a set of trip pins 144 (FIGS. 10–13) disposed in a circular array about the axis 20. The trip pins 144 project axially out of the index disk 100, in a direction indicated by the arrow 112 (FIG. 10).

A trigger base 150 (FIG. 11) is disposed atop the fixed guide 80. Two screws extend down through counterbored screw holes (not shown) in the trigger base 150, into screw holes 152 (FIG. 11) in the fixed guide 80, to secure the trigger base 150 to the fixed guide 80.

Figure 11:
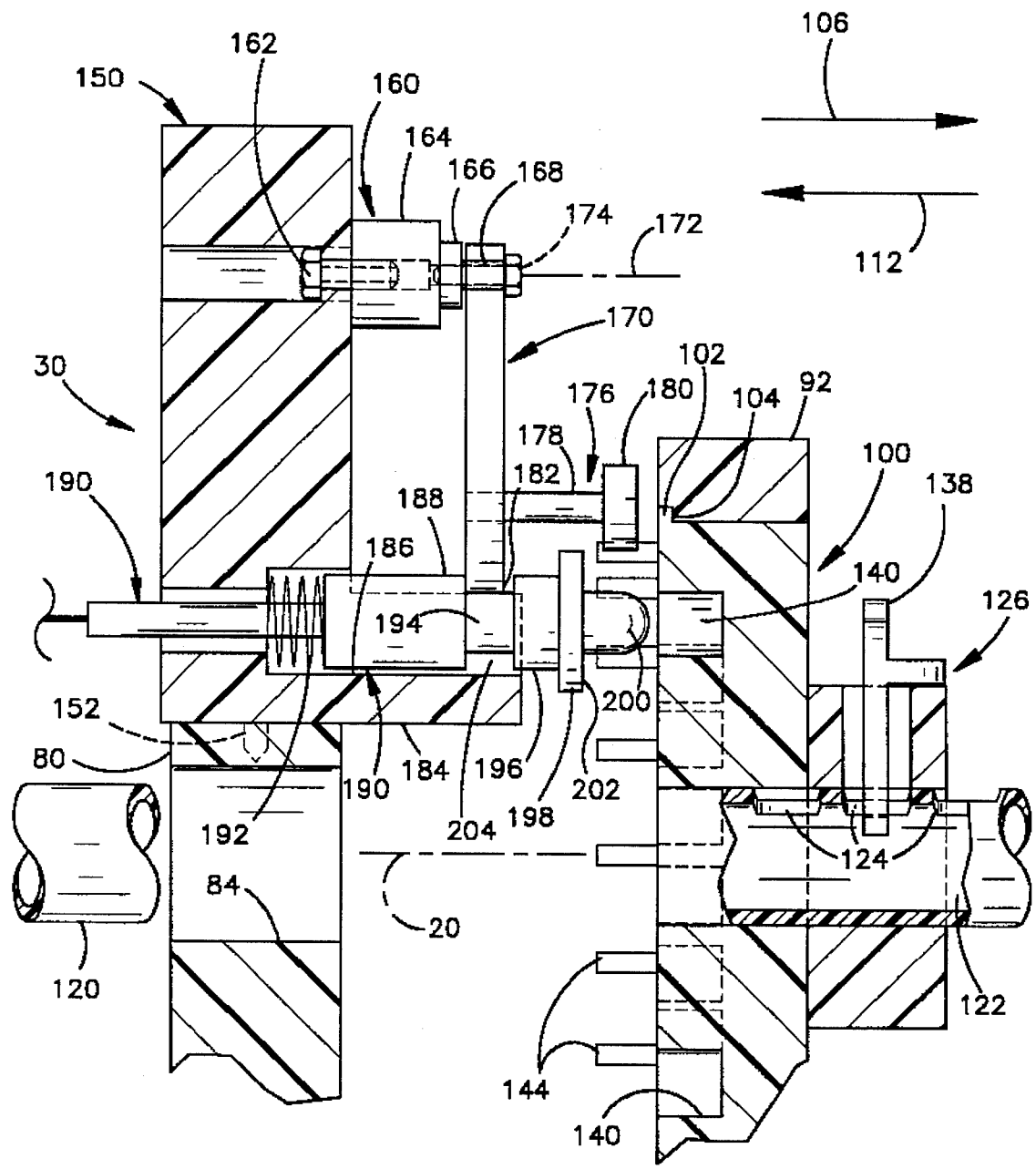
FIG. 11 is an enlarged view of a portion of FIG. 10.

The trigger base 150 supports an arbor 160 (FIG. 11). A screw 162 secures the arbor 160 to the trigger base 150. The arbor 160 has a main body portion 164, an intermediate portion 166, and an end portion 168.

A trigger 170 hangs down from the end portion 168 of the arbor 160 and is supported for swinging movement on the arbor 160 about an axis 172. A screw 174 holds the trigger 170 on the arbor 160. The trigger 170 has a lower end portion 182. A trigger extension 176 projects axially from the trigger 170. The trigger extension 176 includes a shank portion 178 and an outer end portion 180.

The trigger base 150 has a plunger support portion 184 with a cylindrical opening 186 which extends back into the main body of the trigger base 150. A main body portion 188 of a plunger 190 is received in the opening 186. A compression spring 192 biases the plunger 190 in a direction to the right, as indicated by the arrow 106.

The plunger 190 also has a reduced diameter shank portion 194, a second body portion 196, a third body portion 198, and a plunger tip portion 200. The third body portion 198 has a radially extending end face 202 facing toward the index disk 100. The plunger main body portion 188 and the plunger second body portion 196 define between them a longitudinally extending annular gap 204. When the plunger 190 is in the position as shown in FIG. 11, i.e., retracted away from the index disk 100, the lower end portion 182 of the trigger 170 falls into the gap 204 in the plunger 190. The trigger 170 hangs straight down by its own weight.

Figure 18:
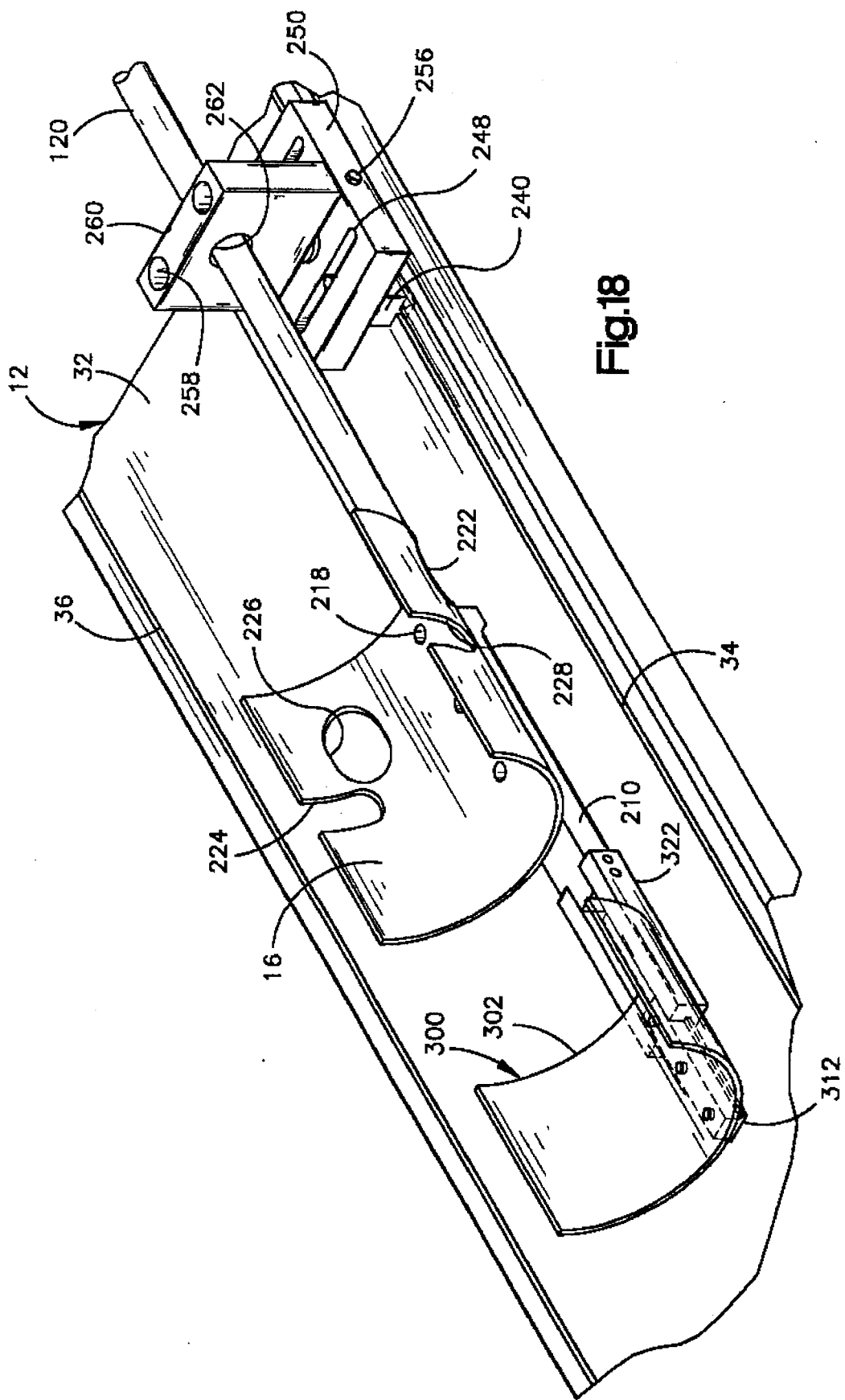
FIG. 18 is a perspective view of the cuff and free guide portions of the apparatus of FIG. 6.

Toward the other end of the index assembly 10, a paddle 210 (FIGS. 18 and 19) has a rounded end portion 212 (FIG. 19) which is press fit into an end portion 214 of the support tube 120. A plurality of screws 216 (only one of which is shown) extend through screw holes 218 in a plastic body portion 220 of the cuff 16. The screws 216 secure the cuff 16 to the paddle 210. The cuff 16 is bent into a semi-cylindrical shape about the axis 20. The cuff 16 has a thumb hole 222 for receiving the right thumb of the patient's hand, and a wrist bone opening 224 to allow room for the patient's wrist bone to extend out of the cuff 16. The cuff 16 also has a similar thumb hole 226 and wrist bone opening 228 for use when the patient's left hand is strapped in the cuff 16.

Two straps 230 extend from the one side of the plastic body portion 220 of the hand cuff 16. On the end of each strap 230 is a D-ring 232. A velcro strap 234 extending from the opposite side of the plastic body portion 220 of the cuff 16, is extensible through the D-ring 232 to secure the patient's hand to the cuff 16. Once the cuff 16 has been secured to the patient's hand, the support tube or rod 120 forms an extension of the patient's arm.

A free guide slider 240 (FIG. 16) has a longitudinally extending rib 242 which fits into one or the other of the grooves 34, 36 in the table 12. The slider 240 has two screw holes 244, spaced apart along the length of the slider, which receive respective screws 246 through respective slots 248 in a free guide base 250. The slots 240 are wider than the diameter of the shank portions of the screws 246. The slots 246 extend in a direction across the width of the table 12.

Thus, when the screws 246 are inserted through the slots 248 into the slider 240, the free guide base 250 is movable across the width of the table 12 via the slots 248.

The free guide base 250 is also slidable along the length of the table 12 via the engagement of the rib 242 in the groove 34 or 36. Two free guide support posts 252 are connected with the free guide base 250 for movement with the free guide base. Each post 252 has a notch 254 near its lower end which receives a set screw 256. The posts 252 thus project upwardly from and are movable with the free guide base 250.

The posts 252 extend through post holes 258 in a free guide 260. The free guide 260 has a central passage 262 for receiving therethrough the support tube 120. Thus, the free guide 260 can move up and down on the posts 252, supporting the support tube 120 for vertical movement relative to the upper major side surface 32 of the table 12. The free guide 260 and the main tube 120 are thus movable in all directions relative to the table 12.

The free guide 120 has a threaded opening 264 which receives the threaded shank portion 266 of a thumb screw 268. The head portion 270 of the thumb screw 268 rides on the upper major side surface 272 of the free guide base 250. Rotation of the thumb screw 268 in the free guide 260 sets a lower limit of the vertical positioning of the free guide 260 on the free guide base 250.

Figure 19:
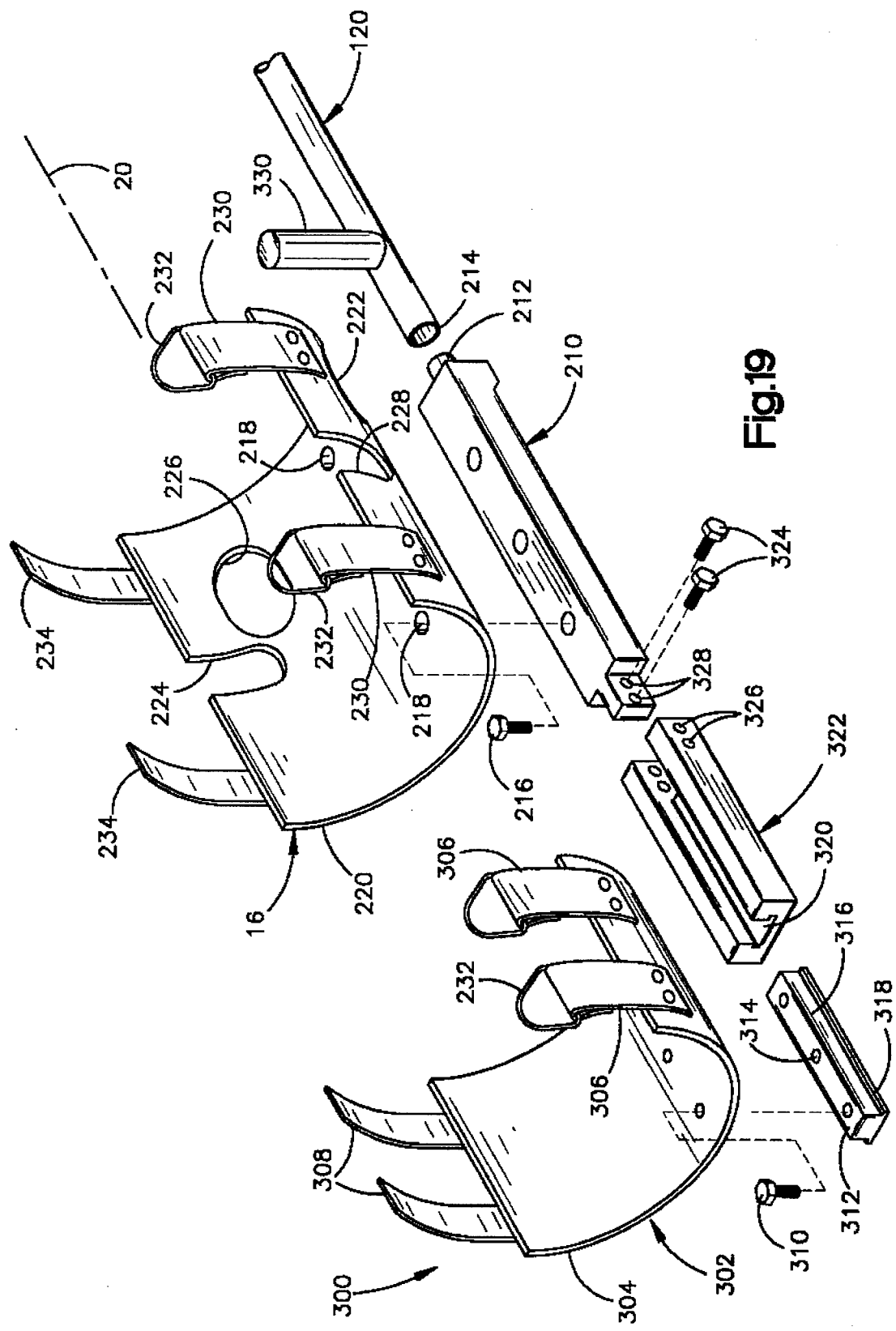
FIG. 19 is an exploded perspective view of the cuff portion of FIG. 18.

In operation of the indexing assembly 10, the patient lies on his back on the imaging table 12, with his head to the left and his feet to the right as viewed in FIGS. 6 and 7. The patient's right hand is secured in the cuff 16, palm up. The patient's right thumb extends through the thumb hole 222 (FIG. 19). The wrist bone may extend outwardly of the plastic body 220 of the cuff 16 through the wrist bone opening 224. The patient's shoulder is inside the shoulder coil 18 (FIG. 6), which is a known secondary imaging coil. The table 12 is then slid axially inside the primary imaging coil 14.

The shoulder may first be imaged in the starting orientation. Then, the patient is instructed to move the shoulder joint to the next orientation. To do this, the patient first pulls on a finger grip 280 (FIG. 8) attached to an actuator cord 282. The actuator cord 282 is connected with the plunger 190. The actuator cord transmits the force of the patient's pulling action to the plunger 190, and the plunger is retracted from the engaged position shown in FIGS. 12 and 13 to the disengaged position shown in FIGS. 10 and 11.

As the plunger is thus retracted, the gap 204 in the plunger moves axially into a position adjacent the lower end portion 182 of the trigger 170 (FIG. 11). The trigger 170 is then free to pivot about the axis 172. The force of gravity causes the trigger 172 to assume a vertical position so that the lower end portion 182 of the trigger moves into the gap 204 in the plunger 190 (FIGS. 12, 13). The trigger 170 then blocks axial movement of the plunger 190 toward the index disk 100. The plunger 190 is thus held away from the index disk 100, and the index disk is free to rotate about the axis 20.

Since the index disk 100 is connected through the main tube 120 with the cuff 16, the cuff 16 is now also free to rotate about the axis 20. The patient can then move his shoulder joint to the next orientation, as desired, by rotating his hand which is secured in the cuff 16. The patient may grasp a handle 330 (FIGS. 6 and 7) which is secured to and forms a portion of the main tube or rotatable member 120 to better assist in rotation of the cuff 16. As the patient rotates his hand, the cuff 16 and the index disk 100 rotate. If the patient is turning his hand inward, the index disk 100 rotates in a clockwise direction as viewed in FIG. 12, as indicated by the arrow 290.

As the index disk 100 rotates, the trip pins 144 and the plunger openings 140 revolve about the axis 20. One of the trip pins designated 292 in FIG. 13, almost immediately engages the trigger extension 180, and pivots the trigger out of the gap 204 in the plunger 190. This allows the plunger 190 to move back toward the index disk 100 under the influence of the plunger spring 192. The plunger tip 200 engages the face of the index disk 100, then falls automatically into the next plunger opening 140 as the index disk 100 continues to rotate. The engagement of the plunger 190 in the plunger opening 140 limits movement of the plunger outwardly from the trigger base 150, in a direction to the right as indicated in FIG. 11.

If more support is needed for the patient's arm, a biceps support assembly 300 (FIGS. 1, 2, 18 and 19), can be provided. The biceps support assembly includes a biceps cuff 302 having a plastic body portion 304 (FIG. 19). Two straps 306 having D-rings thereon extend from one side of the biceps cuff 302. Two velcro straps 308 extend from the other side and can be looped through the D-rings and secured to themselves to clamp the patient's biceps firmly in the plastic body portion 304 of the biceps cuff 302.

A plurality of fasteners 310 (only one of which is shown) secure the plastic body portion 304 on the biceps cuff 302 to a biceps cuff slider 312. The fasteners 310 are received in fastener openings 314 on the upper surface of the biceps slider 312. The biceps slider 312 has a main body portion 316 and a lower lip portion 318. The lip portion 318 is received in a groove 320 in a paddle extension 322. The paddle extension 322 is secured with screws 324 through openings 326 in the paddle extension 322 and through openings 328 in the paddle 210.

The biceps cuff slider 312 is slidable in the groove 320 in the paddle extension 322. Since the paddle 322 is fixed relative to the paddle 210 and the main tube 120, the biceps cuff 302 is thus slidable in a direction parallel to the axis 20, relative to the hand cuff 16. Thus, the patient's biceps can be securely clamped in the biceps cuff assembly 300, to provide additional support and stability for the arm while it is being imaged, yet the biceps cuff assembly is slidable along the length of the table to provide for adjustment and movement during changing orientation.

The cuff 16 (FIGS. 6 and 7) may be placed at different longitudinal positions along the length of the table 12 relative to the index mechanism 30. The main tube 120 has a plurality of slots 124 adjacent the index mechanism 30. The lock pointer 126, as discussed above, is received in a selected one of these slots 124. To accommodate patients of different sizes, the lock pointer 126 may be disengaged from the position shown in FIG. 21, and moved radially outwardly of the main tube 120 so that the main tube 120 may be slid longitudinally along the axis 20 relative to the clamp block 108. When the cuff 16 is at the appropriate location to hold the patient's hand, the lock pointer 126 is inserted through the nearest slot 124 into the main tube 120, and secured therein, as described above.

As discussed above, the free guide 260 (FIG. 16) is relatively movable on the table 12. This movement accommodates shifting movement of the hand cuff 16 upon movement of the patient's hand or shoulder joint. For example, as the patient's hand is rotated inwardly, the arm tends to rise. The free guide 260 allows for this movement, sliding vertically upward along the free guide support posts 252.

The entire index mechanism 30 (FIGS. 6, 7) may be placed in different lateral positions on the table extension 42.

As discussed above, three keyholes 64 (FIG. 9) are provided in the indexer base 60, while five slots 50 are provided in the table extension 42. The indexer base 60 may be secured to the table extension 42 with the hold-down 70 extending through any one of the three keyholes 64 into any one of the slots 52. Thus, a total of fifteen different positions are available for the indexer base 60, laterally across the width of the table extension 42. This can accommodate imaging of patients with different physical characteristics, as well as, of course, imaging of the right or the left hand. For imaging of the left hand, the free guide 260 would be placed in the groove 36 (FIG. 6) on the opposite side of the table 12.

The apparatus 10 may be used in many different ways. The apparatus may be used in association with the imaging table 12 as described herein. However, the apparatus 10 may be used with other known patient support structures, if desired. Thus, the patient could be sitting, standing, or lying when the apparatus 10 is used to image a shoulder joint of the patient. The cuff 16 may be used with or without the biceps support assembly 300. In fact, the cuff 16 and the biceps support assembly 300 may be eliminated and the main tube or rod 120 rotated by force transmitted from the hand of the patient to the handle 330.

It is contemplated that the use of the apparatus 10 may be either patient directed or operator directed. When the use of the apparatus 10 is to be patient directed, force is transmitted from the arm of the patient through the cuff 16 to the tube or rod 120, and/or through the biceps support assembly 300 to the tube or rod 120, and/or through the handle 330 to the tube or rod 120. Thus, the cuff 16, the biceps support assembly 300, and the handle 330 may be used either separately or together to transmit force from the arm of the patient to the tube or rod 120. When the operation of the apparatus 10 is to be patient directed, the patient actuates the index mechanism 30 from an engaged condition to a disengaged condition by pulling on the finger grip 280 to transmit force through the actuator cord 282.

When the apparatus 10 is to be operator directed, the tube or rod 120 is rotated about its central axis under the influence of force applied to the handle at the right (as viewed in FIG. 7) end of the tube or rod 120 by an operator. In the operator directed mode of operation, the index mechanism 30 may be operated from the engaged condition to the disengaged condition by force transmitted to the index mechanism by the operator. Of course, if desired, the patient could use the finger grip 280 to actuate the index mechanism 30 from the engaged condition to the disengaged condition when instructed by the operator. The operator would then apply force to the handle at the end of the rod or tube 120 to rotate the rod or tube after the patient has operated the index mechanism to the disengaged condition.

The foregoing description of the use of the apparatus 10 has been in conjunction the imaging of an arm at a shoulder joint where the arm is connected with a trunk of the patient. However, it should be understood that the apparatus 10 could be used in conjunction with the imaging of a hip joint where the leg of the patient is connected with the trunk of the patient. It should also be understood that the operator could distract either the hip or shoulder joint by pulling on the handle at the right (as viewed in FIG. 7) end of the rod or tube 120 during imaging at some or all of the positions to which the index mechanism 30 is operated.

From the above description of the invention, those skilled in the art will perceive improvements, changes and modifications in the invention. Such improvements, changes and modifications within the skill of the art are intended to be covered by the appended claims.

Having described the invention, the following is claimed:

1. A method of imaging a joint region where a portion of a longitudinally extending limb of a patient is connected with a trunk of the patient, said method comprising the steps of moving at least the joint region of the patient where the limb of the patient is connected with the trunk of the patient into a chamber of an imaging unit, changing the orientation of at least a portion of the joint region of the patient where the limb of the patient is connected with the trunk of the patient while the joint region of the patient is in the imaging unit, said step of changing the orientation of at least a portion of the joint region of the patient includes rotating the limb of the patient connected with the joint region about a longitudinal axis of the limb which extends through the joint region, and imaging the joint region of the patient where the limb of the patient is connected with the trunk of the patient prior to and after performance of said step of rotating the limb about an axis of the limb.

2. A method as set forth in claim 1 further including interconnecting the limb of the patient and a rotatable member, said step of rotating the limb of the patient includes rotating the rotatable member about an axis which extends parallel to the longitudinal axis of the limb while the limb of the patient and the rotatable member are interconnected.

3. A method as set forth in claim 2 wherein said step of interconnecting the limb of the patient and the rotatable member includes gripping the rotatable member with a hand on the limb of the patient.

4. A method as set forth in claim 2 wherein said step of interconnecting the limb of the patient and the rotatable member includes gripping a hand on the limb of the patient with an apparatus connected with the rotatable member.

5. A method as set forth in claim 2 wherein said step of rotating the rotatable member includes rotating the rotatable member under the influence of force transmitted from the limb of the patient to the rotatable member.

6. A method as set forth in claim 2 wherein said step of rotating the rotatable member includes rotating the rotatable member under the influence of force transmitted to the rotatable member from a source of force other than the patient.

7. A method as set forth in claim 2 wherein said step of interconnecting the limb of the patient and the rotatable member includes gripping the limb of the patient with an apparatus connected with the rotatable member.

8. A method as set forth in claim 2 wherein said step of interconnecting the limb of the patient and the rotatable member includes gripping an arm of the patient with an apparatus connected with the rotatable member.

9. A method as set forth in claim 2 wherein said step of interconnecting the limb of the patient and the rotatable member includes gripping a leg of the patient with an apparatus connected with the rotatable member.

10. A method as set forth in claim 2 further including the step of supporting the patient on a support surface, said step of rotating the rotatable member includes rotating the rotatable member about an axis which extends parallel to the support surface.

11. A method as set forth in claim 10 further including moving the rotatable member relative to the support surface to vary the distance between the axis of rotation of the rotatable member and the support surface while maintaining the axis of rotation of the rotatable member parallel to the support surface during performance of said step of rotating the rotatable member.

12. A method as set forth in claim 2 further including the step of distracting the joint where the upper portion of the limb is connected to the trunk of the patient by applying an axially directed force to the rotatable member.

13. A method of imaging a shoulder joint region where an upper portion of an arm of a patient is connected with a trunk of the patient, said method comprising the steps of connecting the arm of the patient with an elongated member which forms an extension of the arm of the patient and which extends to an index assembly, positioning at least the shoulder joint region of the patient in an imaging unit, thereafter, imaging the shoulder joint region of the patient with the elongated member in a first index position, thereafter, changing the orientation of at least a portion of the shoulder joint region of the patient by rotating the elongated member and the arm of the patient about a longitudinal axis of the elongated member while the shoulder joint region is in the imaging unit, retaining the elongated member and the arm of the patient against rotation with the index assembly upon rotation of the elongated member from the first index position to a second index position, thereafter, imaging the shoulder joint region of the patient while the elongated member is retained in the second index position by the index assembly.

14. A method as set forth in claim 13 further including the steps of operating the index assembly from an engaged condition retaining the elongated member in the first index position to a disengaged condition releasing the elongated member for rotation from the first index position to the second index position after having performed said step of imaging the shoulder joint region of the patient with the elongated member in the first index position, said step of operating the index assembly from the engaged condition to the disengaged condition being performed under the influence of force transmitted from the patient to the index assembly.

15. A method as set forth in claim 13 wherein the step of rotating the elongated member about a longitudinal axis of the elongated member is performed under the influence of force transmitted from the arm of the patient to the elongated member.

16. A method as set forth in claim 13 further including the step of applying force to the elongated member at a location adjacent to the index assembly during performance of said step of imaging the shoulder joint region of the patient while the elongated member is retained in the second index position to move the elongated member in axial direction and distract the shoulder joint of the patient under the influence of force transmitted through the elongated member.

17. A method as set forth in claim 13 further including the step of moving at least a portion of the elongated member in a direction transverse to the longitudinal axis of the elongated member under the influence of force transmitted to the elongated member from the arm of the patient during rotation of the elongated member.

18. A method as set forth in claim 13 further including the step of distracting the shoulder joint of the patient during performance of said step of imaging the shoulder joint region of the patient with the elongated member in the first index position.

19. A method as set forth in claim 13 wherein said step of connecting the arm of the patient with the elongated member includes gripping a hand of the patient with a cuff which is connected with the elongated member, said step of rotating the elongated member including transmitting force applied against the cuff by the hand of the patient to the elongated member to rotate the elongated member.

20. A method as set forth in claim 13 wherein said step of connecting the arm of the patient with the elongated member includes gripping a portion of the arm of the patient with a cuff which is connected with the elongated member, said step of rotating the elongated member including transmitting force applied against the cuff by the arm of the patient to the elongated member to rotate the elongated member.

21. A method as set forth in claim 13 further including gripping a projection connected with the elongated member with a hand on the arm of the patient, said step of rotating the elongated member includes rotating the elongated member under the influence of force transmitted to the elongated member through the hand of the patient.

22. A method of imaging a joint region where a limb of a patient is connected with a trunk of the patient, said method comprising the steps of gripping a portion of the limb of the patient with a cuff, moving at least the joint region of the patient into an imaging unit, changing the orientation of at least a portion of the joint region of the patient where the limb of the patient is connected with the trunk of the patient while the joint region is in the imaging unit, said step of changing the orientation of the joint region includes moving the cuff from a first position to a second position relative to the trunk of the patient while the joint region is in the imaging unit, imaging the joint region when the cuff is in the first position, imaging the joint region when the cuff is in the second position, and applying force to the cuff when the cuff is in said first and second positions to distract a joint in the joint region during imaging of the joint region, said step of applying force to the cuff includes pulling the cuff in a direction away from the joint region and generally parallel to a longitudinal axis of the limb of the patient during imaging of the joint region when the cuff is in the first and second positions.

23. A method as set forth in claim 22 wherein said step of moving the cuff from a first position to a second position includes rotating the limb of the patient about an axis of the limb which extends through the joint region.

24. A method as set forth in claim 22 wherein said step of moving the cuff from a first position to a second position includes moving the cuff along an arcuate path in the imaging unit under the influence of force applied against the cuff by the limb of the patient, transmitting force applied against the cuff by the limb of the patient to an elongated member connected with the cuff to rotate the elongated member about a longitudinal axis extending through the elongated member, and simultaneously therewith utilizing the elongated member to retain the cuff against movement away from the arcuate path.

25. A method as set forth in claim 22 wherein said step of moving the cuff includes rotating the cuff and the portion of the limb gripped by the cuff about an axis extending through the joint region where the upper portion of the limb is connected with the trunk of the patient, said method further including operating a detent to an engaged condition to maintain the cuff in the first position during imaging of the joint region with the cuff in the first position, operating the detent to a released condition under the influence of force applied to the cuff by the limb of the patient to release the cuff for rotational movement about the axis extending through the joint region.

26. A method as set forth in claim 22 wherein said step of moving the cuff from a first position to a second position includes moving the cuff along an arcuate path in the imaging unit under the influence of force applied against the cuff from a source of force other than the patient.

27. A method as set forth in claim 22 wherein said step of moving the cuff includes rotating the cuff and the portion of the limb gripped by the cuff about an axis extending through the joint region where the upper portion of the limb is connected with the trunk of the patient, said method further including operating a detent to an engaged condition to maintain the cuff in the first position during imaging of the joint region with the cuff in the first position, operating the detent to a released condition under the influence of force from a source other than the patient to release the cuff for rotational movement about the axis extending through the joint region.

28. A method of imaging a joint region where an upper portion of a longitudinally extending limb of a patient is connected with a trunk of the patient, said method comprising the steps of gripping a portion of the limb of the patient with a cuff, moving at least the joint region of the patient into an imaging unit while gripping the limb of the patient with the cuff, rotating the limb of the patient and the cuff about a longitudinal central axis of the limb of the patient to move the cuff to a first predetermined position while the joint region is in the imaging unit, operating a detent to an engaged condition upon movement of the cuff to the first predetermined position to maintain the cuff in the first predetermined position, imaging the joint region of the patient while the joint region is in the imaging unit and the cuff is in the first predetermined position with the detent in the engaged condition, operating the detent from the engaged condition to a released condition after having performed said step of imaging the joint region while the cuff is in the first predetermined position, resuming rotation of the limb of the patient and the cuff about a longitudinal central axis of the limb of the patient to move the cuff to a second predetermined position while the joint region is in the imaging unit, operating the detent to an engaged condition upon movement of the cuff to the second predetermined position to maintain the cuff in the second predetermined position, and imaging the joint region of the patient while the joint region is in the imaging unit and the cuff is in the second predetermined position with the detent in the engaged condition.

29. A method as set forth in claim 28 wherein said step of rotating the limb of the patient and the cuff about the central axis of the limb includes rotating the cuff under the influence of force transmitted to the cuff from the limb of the patient.

30. A method as set forth in claim 28 wherein said step of operating the detent from the engaged condition to the released condition includes operating the detent under the influence of force transmitted from the limb of the patient and through the cuff.

31. A method as set forth in claim 28 wherein said step of operating the detent from the engaged condition to the released condition includes operating the detent under the influence of force which is transmitted along a path which is spaced from the cuff.

32. A method as set forth in claim 28 wherein said step of gripping a portion of the limb of the patient with a cuff includes connecting the limb of the patient with a cuff and with an elongated member which forms an extension of the limb of the patient and which extends to an index assembly in which the detent is located.

33. A method as set forth in claim 28 wherein said step of rotating the limb of the patient and the cuff about the central axis of the limb includes rotating the cuff under the influence of force transmitted to the cuff from a source of force other than the patient.

34. A method as set forth in claim 28 wherein said step of gripping a portion of the limb of the patient with a cuff includes connecting the limb of the patient with a cuff and with an elongated member which forms an extension of the limb of the patient and which extends to an index assembly in which the detent is located, said step of rotating the limb of the patient and the cuff about the central axis of the limb includes rotating the cuff under the influence of force transmitted to the cuff from the rotatable member.

35. A method of imaging a shoulder joint region where an upper portion of an arm of a patient is connected with a trunk of the patient, said method comprising the steps of gripping a portion of a rotatable member with a hand on the arm of the patient, moving at least the shoulder joint region of the patient into an imaging unit, rotating the hand and arm of the patient and the rotatable member about a longitudinal central axis of the arm of the patient to rotate the rotatable member while the shoulder joint region is in the imaging unit and while the hand of the patient is gripping the rotatable member, and imaging the shoulder joint region while the shoulder joint region is in the imaging unit and the hand of the patient is gripping the rotatable member.

36. A method as set forth in claim 35 wherein said step of rotating the hand and arm of the patient and the rotatable member about a central axis of the arm of the patient includes rotating the rotatable member under the influence of force transmitted to the rotatable member from the hand of the patient.

37. A method as set forth in claim 35 wherein said step of rotating the hand and arm of the patient and the rotatable member about a central axis of the arm of the patient includes rotating the hand and arm of the patient under the influence of force transmitted to the hand of the patient from the rotatable member.

38. A method as set forth in claim 35 further including the steps of operating a detent to an engaged condition upon rotation of the rotatable member to a first predetermined position to interrupt rotation of the rotatable member and maintain the rotatable member in the first predetermined position, operating the detent from the engaged condition to a release condition after imaging the shoulder joint region while the rotatable member is in the first position, and operating the detent to the engaged condition upon rotation of the rotatable member to a second predetermined position to interrupt rotation of the rotatable member and maintain the rotatable member in the second predetermined position.

39. A method as set forth in claim 38 wherein said step of operating the detent from the engaged condition to the released condition includes operating the detent under the influence of force transmitted from the patient to the rotatable member.

40. A method as set forth in claim 38 wherein said step of operating the detent from the engaged condition to the released condition includes operating the detent under the influence of force which is transmitted to the detent along a path which is spaced from the rotatable member.

41. A method as set forth in claim 38 wherein said step of rotating the rotatable member includes rotating a rotatable member which extends along the body of the patient past the feet of the patient to an index assembly in which the detent is located.

42. A method of imaging a joint region where a limb of a patient is connected with a trunk of the patient, said method comprising the steps of gripping a portion of the limb of the patient with a cuff, moving at least the joint region where the limb of the patient is connected with the trunk of the patient into an imaging unit, thereafter, changing the orientation of at least a portion of the joint region where the limb of the patient is connected with the trunk of the patient while the joint region is in the imaging unit, sequentially imaging the joint region while the joint region is in a plurality of different orientations in the imaging unit, and applying force to the cuff to distract a joint in the joint region during imaging of the joint region while the joint region is in each of the plurality of different orientations in the imaging unit, said step of applying force to the cuff includes pulling the cuff in a direction away from the joint region and parallel to a longitudinal axis of the limb of the patient during imaging of the joint region while the joint region is in each of the plurality of different orientations in the imaging unit.

43. A method as set forth in claim 42 wherein said step of changing the orientation of at least a portion of the joint region where the limb of the patient is connected with the trunk of the patient while the joint region is in the imaging unit includes rotating a member connected with the cuff about the longitudinal axis of the limb of the patient, said step of pulling the cuff in a direction away from the joint region and parallel to the longitudinal axis of the limb of the patient includes pulling on the member connected with the cuff.

44. A method as set forth in claim 42 wherein said step of changing the orientation of at least a portion of the joint region includes moving the cuff from a first position to a second position relative to the trunk of the patient, said step of sequentially imaging the joint region includes imaging the joint region when the cuff is in the first position relative to the trunk of the patient and imaging the joint region when the cuff is in the second position relative to the trunk of the patient.

* * * * *